United States Patent
Menges et al.

(10) Patent No.: US 9,229,000 B2
(45) Date of Patent: Jan. 5, 2016

(54) SINGLE-STEP MULTIPLEX IMMUNOASSAY

(75) Inventors: Friedrich Menges, Jena (DE); Jenny Zahringer, Arnstadt (DE)

(73) Assignee: ZENTERIS GMBH (DE)

( * ) Notice: Subject to any disclaimer, the term of this patent is extended or adjusted under 35 U.S.C. 154(b) by 754 days.

(21) Appl. No.: 12/740,569

(22) PCT Filed: Nov. 3, 2008

(86) PCT No.: PCT/EP2008/009249
§ 371 (c)(1),
(2), (4) Date: Jul. 27, 2010

(87) PCT Pub. No.: WO2009/056350
PCT Pub. Date: May 7, 2009

(65) Prior Publication Data
US 2010/0285986 A1 Nov. 11, 2010

(30) Foreign Application Priority Data
Nov. 2, 2007 (DE) .......................... 10 2007 052 281

(51) Int. Cl.
*B01L 3/00* (2006.01)
*G01N 33/543* (2006.01)

(52) U.S. Cl.
CPC ........ *G01N 33/54366* (2013.01); *B01L 3/5027* (2013.01); *B01L 3/50273* (2013.01); *B01L 3/502715* (2013.01); *B01L 3/502738* (2013.01); *G01N 33/54386* (2013.01); *G01N 33/54393* (2013.01); *B01J 2219/0074* (2013.01); *B01J 2219/00387* (2013.01); *B01J 2219/00547* (2013.01); *B01J 2219/00576* (2013.01); *B01J 2219/00605* (2013.01); *B01J 2219/00612* (2013.01); *B01J 2219/00637* (2013.01); *B01J 2219/00693* (2013.01);

(Continued)

(58) Field of Classification Search
USPC .................. 422/501–504, 549, 554, 109; 435/287.1–287.3, 287.9, 288.1–288.7, 435/808, 810, 973, 975; 436/155, 156, 514, 436/539, 540, 52, 147, 180
See application file for complete search history.

(56) References Cited

U.S. PATENT DOCUMENTS 4,584,268 A * 4/1986 Ceriani et al. ............... 435/7.23
7,531,169 B2 * 5/2009 Singh et al. ................. 424/130.1

(Continued)

FOREIGN PATENT DOCUMENTS

WO    WO02090983    11/2002
WO    WO2005108604  11/2005

(Continued)

OTHER PUBLICATIONS

Ligler, F.S. The Array Biosensor: Portable, Automated Systems, *Analytical Sciences*, Jan. 2007, vol. 23, pp. 5-10.

*Primary Examiner* — Bao-Thuy Nguyen
*Assistant Examiner* — Erik B Crawford
(74) *Attorney, Agent, or Firm* — Marianne Fuierer; Moore & Van Allen, PLLC

(57) ABSTRACT

The present invention relates to a system and a method for the immunological detection of several substances or a substance having several features in one step, the detection reaction being based on an immunological sandwich type method and being in particular characterized in that it can easily be carry out and is designed as a "one-pot method", which means that all detection steps are carried out in one reaction batch without any wash steps and with only one addition of reagents.

8 Claims, 21 Drawing Sheets

(52) U.S. Cl.
CPC ............... *B01J 2219/00725* (2013.01); *B01L 2300/0636* (2013.01); *B01L 2300/0816* (2013.01); *B01L 2300/0819* (2013.01); *B01L 2300/0877* (2013.01); *B01L 2300/18* (2013.01); *B01L 2400/0481* (2013.01); *B01L 2400/0487* (2013.01)

(56) References Cited

U.S. PATENT DOCUMENTS

| | | | |
|---|---|---|---|
| 7,723,123 B1 * | 5/2010 | Murphy et al. | 436/514 |
| 2002/0150933 A1 * | 10/2002 | Ehricht et al. | 435/6 |
| 2003/0175774 A1 * | 9/2003 | Hunkapiller et al. | 435/6 |
| 2004/0137607 A1 * | 7/2004 | Tanaami et al. | 435/287.2 |
| 2004/0209236 A1 * | 10/2004 | DePablo et al. | 435/1.1 |
| 2006/0078929 A1 * | 4/2006 | Bickel et al. | 435/6 |
| 2007/0254372 A1 | 11/2007 | Bickel et al. | |

FOREIGN PATENT DOCUMENTS

| | | |
|---|---|---|
| WO | WO2006132666 | 12/2006 |
| WO | WO2007051861 | 5/2007 |
| WO | WO2007051863 | 5/2007 |
| WO | WO2007135091 | 11/2007 |
| WO | WO2008064865 | 6/2008 |

* cited by examiner

Fig. 13:

| No. | Code | Antigen | Art | Antibody |
|---|---|---|---|---|
| 1 | R2 | Ricin A | mAK | RCH1 |
| 2 | R20 | Ricin A | pAK | H22 IgY Pool1 (chicken) |
| 3 | S3 | SEB | mAK | BM1323 (mouse) |
| 4 | S12 | SEB | pAK | S9008 (rabbit) |
| 5 | B14 | BoNT/A | pAK | Horse anti-A,B+E |
| 6 | B47 | BoNT/A | | Rabbit anti-A |
| 7 | B56 | BoNT/B | | mAK 1370/6/16 (mouse) |
| | | | | |
| 9 | N11 | Negativ-Ktr. | / | pAKs Serum mouse |
| 10 | N13 | Negativ-Ktr. | / | pAKs Serum rabbit |
| 11 | N14 | Negativ-Ktr. | / | pAKs Serum chicken |
| 12 | N16 | Negativ-Ktr. | / | pAKs Serum horse |
| 13 | M1 | Marker Cy5 | / | Cy5-CCTCTGCAGACTACTATTAC |

Fig. 14:

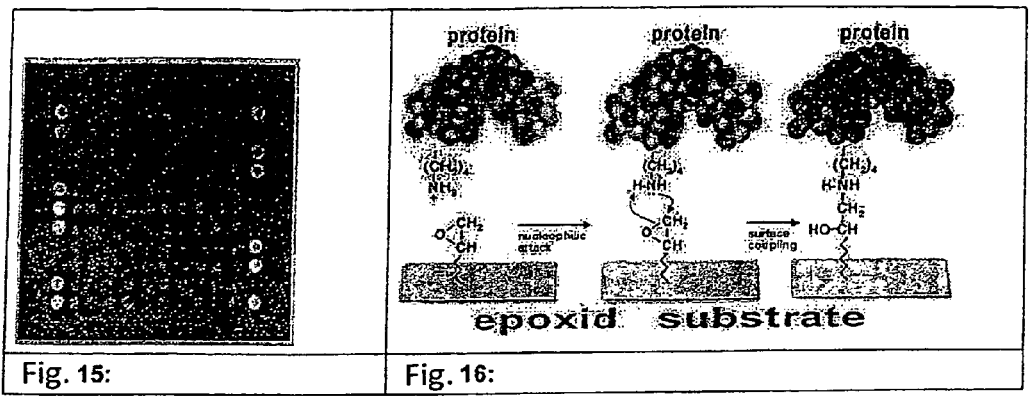
Fig. 15:
Fig. 16:
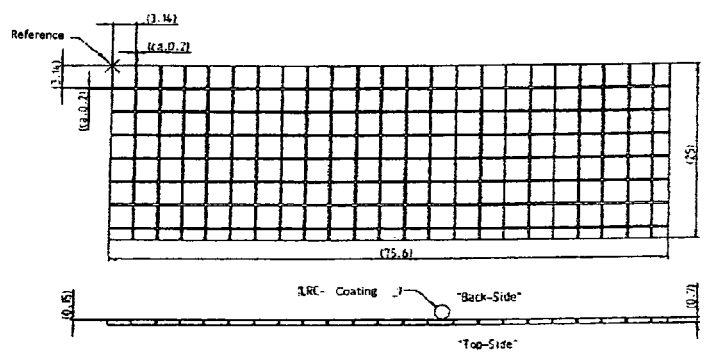
Fig. 17:

Fig. 20

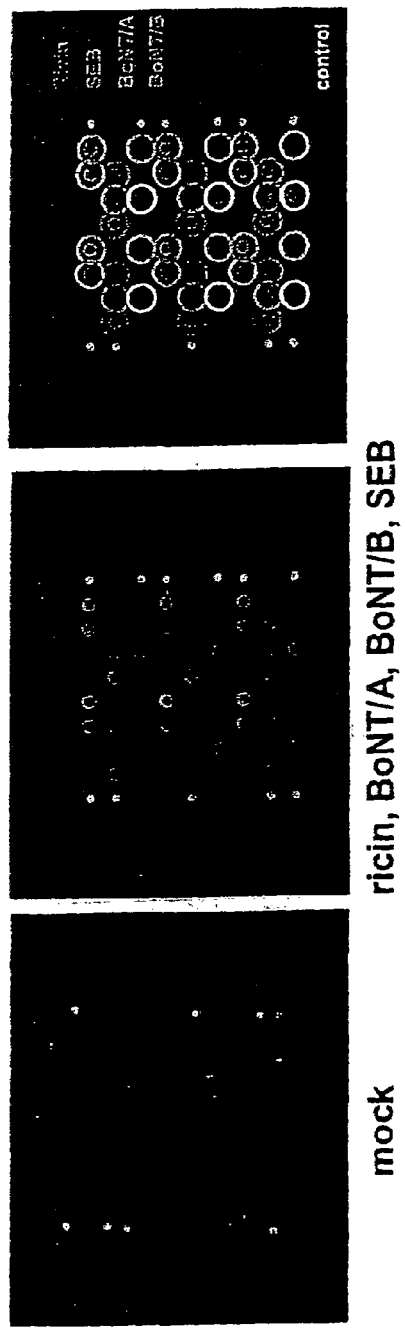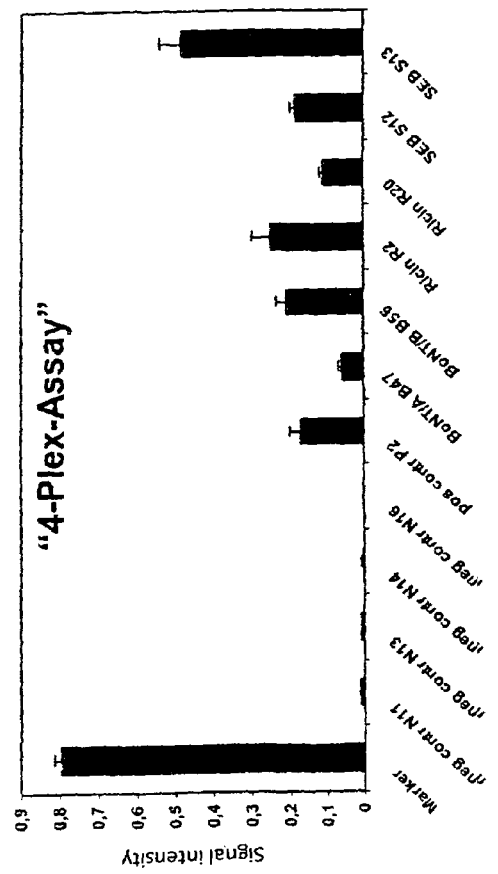
FIG. 22

Fig. 23

SINGLE-STEP MULTIPLEX IMMUNOASSAY

CROSS-REFERENCE TO RELATED APPLICATIONS

This application is filed under the provisions of 35 U.S.C. §371 and claims the priority of International Patent Application No. PCT/EP 2008/009249 filed on Nov. 3, 2008, which in turn claims priority of German Application No. 102007052281.0 filed on Nov. 2, 2007, the contents of which are incorporated by reference herein for all purposes.

TECHNICAL FIELD

The present invention relates to a system and a method for the immunological detection in one step of several substances or of one substance having several features, the detection reaction being based on a sandwich-type immunoassay and being distinguished particularly in that it can easily be carried out and is designed as a "one-pot reaction", which means that all of the detection steps are performed in one reaction batch without rinsing steps and with only one addition of reagents.

BACKGROUND OF THE INVENTION

Related Art

Immunoassays, enzyme-linked immunoassays (ELISA), immunoassays linked by means of fluorescence labeling (FLISA), or immunoassays labeled differently have meanwhile been used as a matter of routine in diagnostic routine work and research for the detection and quantification of proteins, such as antigens, ligands, receptors, antibodies, as well as of chemical compounds.

In an "indirect immunoassay", the protein to be detected, i.e. the antigen (AG), is bound to a solid support, e.g. a polystyrene microtiter plate, by means of adsorption. After a wash step, a specific binding partner, the so-called detection antibody (DAK), is added.

In the "sandwich immunoassay", an antigen-specific binding partner, the so-called capture antibody (FAK), is first adsorbed to the solid support. After a wash step, the sample can be added, and after a further wash step, the DAK can then be added. This method offers the advantage that the FAK selectively captures the antigen from the sample solution so that clearly smaller amounts can be detected.

In the "enzyme-linked immunosorbent assay" (ELISA), an enzyme is linked to the DAKs, said enzyme catalyzing a color reaction in a third step (e.g. horseradish peroxidase (HRP)+ tetramethylbenzidine (TMB)) so as to signal a positive test result.

In the "fluorescent labeled immunoassay" (FLISA), the DAKs are provided either directly with a fluorescent label or with a further binding partner to which a secondary detection system can be bound (e.g. biotin label+Cy5 streptavidin).

When a "sandwich ELISA" or "sandwich FLISA" is carried out, it is common practice to attach the FAKs to a solid support by way of adsorption and to add the further reagents that are required for the test procedure as separate components to the test kits. These reagents are commonly a standard dilution medium and a sample dilution medium, the second specific binding partner (=DAK) in coupled form (i.e. conjugate) as a concentrate or working solution, and, if necessary, a secondary detection system. An assay buffer that is usually present in the form of a concentrate is available for the production of the working solutions for the second specific binding partner as well as for the secondary reagent. Since wash steps are required between the work steps, a conventional immunoassay kit also contains a wash buffer, commonly in concentrated form.

The need to carry out several wash steps in one immunoassay, regardless of the detection principle on which this is based, often causes the tests to be time-consuming and staff-intensive. Each wash step must be understood to be a differentiation step which, depending on the type of molecule, shows different results in terms of duration, intensity, temperature and medium composition and which above all does not allow an optimum reaction equilibrium to be set. This results in clear disadvantages as regards reproducibility, multiplex possibilities, duration, sample throughput, automation and costs.

However, already described in WO 02/090983 A2 is a form of an immunoassay which is easier to use and which only comprises one wash step rather than several. Adsorbed on the support (e.g. microtiter plate) is not only the FAK but also the DAK in lyophilized form and possibly the enzyme coupled thereto. The sample to be determined only needs to be added to the assay buffer, by means of which the lyophilisate is reconstituted and the sandwich consisting of FAK, AG and DAK is built up in one step. However, this is then followed by a wash step and the sequential addition of the substrate solution and stop solutions in the case of an enzymatic color reaction. Therefore, it is not possible to refer to an equilibrium sandwich reaction. As is common practice, the quantification is carried out in a plate reader. However, no "real" parallel reaction takes place and thus comparability of the reactions is not ensured, which considerably reduces the reproducibility of the assay. However, in terms of desired automation, increased sample throughput and costs, this method already represents an improvement with respect to the ELISA standard.

The automated detection of molecular interactions between several molecules is described in the patent applications DE 10 2005 052 752 A1, DE 10 2005 052 713 A1 and WO 07/0 51 861 A1 of the Clondiag company. These applications are, however, limited to the detection of nucleic acids.

SUMMARY OF THE INVENTION

It is therefore the object of the present invention to provide a method for the immunological detection in one step of several substances or of one substance having several features, which distinguishes itself particularly in that all of the detection steps are performed in one reaction batch without rinsing steps and with only one addition of reagents.

The inventors have found that the simultaneous immunological detection of several substances or features to be detected (e.g. of an antibody having several specificities) can be carried out by way of multiplex detection using a biochip (also called microarray, chip, protein (bio)chip, probe array). The required biochemical reactions and the detection take place in a cartridge after filling this once with all of the reagents and without any further intervention by the user, i.e. in a "one-tube" reaction or also "one-pot reaction". This requires the establishment of an immunological detection process in which all detection steps are performed in one reaction batch without rinsing steps and subsequent addition of reagents. The layout for the protein biochip clearly defines which binding partner (e.g., antibody) is situated in which site (spot). The layout is deposited in a software and is retrieved after the recording of an image for data analysis. When the substances to be detected that are contained in the sample (e.g. antigens) specifically react with a detection partner (e.g. detection antibody) and bind to the associated capture partner (e.g. capture antibody) on the protein biochip, a measurable signal is generated by the coupled label (e.g. fluorescent dye). It is then possible via the layout to accurately determine the binding partner (e.g. antibody) which is concerned and to draw conclusions to the substance to be detected.

The invention is used for the simultaneous detection of a plurality of substances or features (multiplex format) on the basis of a sandwich detection principle (e.g. ELISA, indirect or competitive detection). In particular, the test can be used for the detection of proteins (e.g. antigens, antibodies), ligands, receptors, steroids, chemical substances, medicaments, toxins, bacteria, viruses and similar substances. For example, it is also suited for the determination of vaccination titers; and it is in particular suited for the multiplex detection of toxins, mycotoxins, bacteria and viruses that might be used as bioweapons, notably ricin, Staphylococcus enteroxin B (SEB), botulism toxins A and B.

The reaction complex is detected by measuring the intensity of a label. In this connection, the label can be applied to the detection binding partner (e.g. detection antibody) either directly or by means of a directly coupled enzyme (e.g. horseradish peroxidase, alkaline phosphatase, and the like) or via an enzymatic reaction that takes place via a secondary step (biotin Streptavidin HRP, neuramidine, dioxigenin/antidioxigenin, enzyme-coupled antibodies against the detection antibody and the like). It is possible to use any label which can be coupled directly to the reaction complex or to a secondary partner and is suitable for carrying out an immunoassay, such as fluorochrome, chemiluminescent labels, radioactive labels and the like.

The biochemical reagent mixtures used in this method, the temperatures to be set for the reactions to occur, and a final evaluation algorithm are explained below on the basis of the selection of an antigen detection via an antibody-antigen-antibody reaction and a fluorescence measurement as the detection label; however, as pointed out above, this is not the only possibility and should not be considered to have a limiting effect.

In summary, the method proceeds as follows:

1. If available in solid form, the sample containing the substances to be detected is taken up in a suitable buffer and is added to the biotest mixture tube. Where the sample is already in liquid form, it can be added immediately to the biotest mixture.

2. This mixture is introduced into the sample space of a cartridge by means of a pipette.

3. The cartridge is placed into the device and the process is started.

4. The cartridge is processed. The process parameters are encoded in the cartridge and deposited in the software, it being possible to target temperatures ranging from room temperature to 100° C. for any desired time intervals.

5. Once the incubation has been completed, the liquid above the biochip is mechanically displaced and an image is taken in the fluorescence channel.

6. Using the array layout, the software evaluates the spot intensities and provides information on the presence of the antigens to be detected in the sample.

Steps 4 to 6 take place in a fully automated manner.

The entire detection system consists of:
a biotest mixture tube for setting up the detection;
a single-use cartridge for receiving the sample;
an apparatus for processing the cartridge;
software for processing and evaluation.

Thus, one component of the test is a prefabricated tube containing the DAKs required for the detection, the antibody(ies) and/or the antigen(s) of the positive control and any other buffer components in lyophilized form or in liquid (aqueous) form (biotest mixture). The DAKs may be fluorescent-labeled, and it is also possible to set up a detection cascade by means of a further binding step (e.g. biotin-labeled DAK and fluorescent-labeled streptavidin); in this case all of the reagents required for this are then components of the biotest mixture as well.

The biotest mixture preferably contains an assay buffer system as is customary in immunology (e.g. PBS buffer), at least one protein for stabilization (e.g. bovine serum albumin) and detection antibodies (directly fluorescent-labeled or, where appropriate, biotinylated). If the detection antibody is biotinylated, the biotest mixture further contains as a positive control a streptavidin-labeled fluorescent dye (for the sandwich detection). Furthermore, the biotest mixture contains antibodies (e.g. interleukin-12—antibodies) which serve as a "model system" to verify the functional capability of the biological system. Where there is a successful antibody-antigen-antibody interaction (murine interleukin-12—interleukin-12—anti-mouse interleukin-12) during processing, a fluorescent signal is produced which demonstrates the functional capability as a positive control. If the biotest mixture is liquid, it further contains at least one detergent, preferably Triton X (e.g. Triton X-100 or Triton X-50). If the biotest mixture is available in lyophilized form, the detergent(s) is (are) contained in a reconstitution solution (aqueous assay buffer) that is to receive the lyophilisate.

TABLE 1

Preferred composition of the biotest mixture (detection antibody mixture)

| Substance | Origin |
| --- | --- |
| PBS buffer | Commercially available as standardized products |
| BSA (bovine serum albumin) | Commercially available as standardized products |
| Fluorescence-labeled detection antibodies (DyLight 649) | Own development or commercially available |
| Positive control (e.g. murine interleukin-12, anti-mouse interleukin-12) | Commercially available as standardized products |
| Stabilizer (e.g. trehalose) | Commercially available |

A stabilizer is preferably added because the macromolecules (e.g., antigen, antibody) are very vulnerable when not in their natural environment. Especially when the spots on the biochip dry up, the activity can be drastically reduced. Thus, it has been found that trehalose has a protective effect on stability and activity in the biotest mixture. As a result of the introduction of crystal water during the drying process, the trehalose matrix offers maximum protection. What is obtained is the hydrate envelope and the native conformation of the proteins, which increases stability.

Various commercially available antibodies (monoclonal and/or polyclonal) that can be used for the detection reaction already exist for the majority of antigens to be detected (e.g., toxins, bacteria, viruses). When it comes to the establishment of the multiplex detection, the selection of suitable antibodies is a key process for preventing cross-reactions which may occur to an increased extent owing to the system properties since wash steps are deliberately dispensed with here. However, since wash steps are dispensed with in the present immunological detection method, the antibodies may be perfectly less "robust" than in the common microtiter plate ELISA. The use of monoclonal antibodies is preferred. It is in particular due to the use of monoclonal antibodies as detection antibodies, i.e. in the biotest mixture, that an increase in signal intensity can be achieved as compared to the use of polyclonal antibodies since monoclonal antibodies only have one epitope and thus also bind only one antigen. When polyclonal antibodies are used, several antigens can also bind to this antibody which is, however, coupled to only a single fluorescent molecule, i.e. the signal strength could be lower.

The components of the biotest mixture are mixed together in corresponding concentrations and admixed with the correspondingly prepared sample for the detection reaction.

A preferred final composition of the biotest mixture contains:

| Component | most preferred concentration | Preferred concentration range |
| --- | --- | --- |
| Triton X | 0.25% | 0.05-2% |
| BSA | 0.5% | 0.1-1.5% |
| PBS | 10 mM | 5-25 mM |
| Trehalose | 100 mM | 20-200 mM |
| IL-12 | 50 ng/ml | 10-200 ng/ml |
| DAK | 1-10 µg/ml (depending on AK) | 05-30 µg/ml (depending on AK) |

In the case of a sandwich ELISA, the actual immunoassay proceeds such that capture antibodies which recognize and bind specifically determined antigens in the sample liquid to be analyzed, are immobilized in spots on the biochip. The reaction solution contains detection antibodies which recognize and bind specifically determined antigens in the sample to be analyzed and which are coupled directly or indirectly to a dye. The sample is mixed with the reaction solution and introduced into the reaction space by means of biochip. Under the influence of a defined temperature profile, the antigens of the sample to be analyzed bind specifically to the corresponding capture antibodies on the biochip surface. Thus, a molecular complex referred to as "sandwich", which consists of immobilized capture antibody, bound sample antigen and detection antibody with dye, forms on the spots on the chip surface (FIG. 13). The "layout" of another immunological detection test is analogous and is managed by a person skilled in the art.

The immunoassay takes place in a sealed compartment (sample space) in which defined temperatures between room temperature and 100° C. can be generated. The sample space is a constituent of a single-use cartridge.

A further constituent of the sample space is a solid support (biochip) on which the FAKs are immobilized. The biochip may consist of, for example, glass, polypropylene, polycarbonate, polystyrene and/or PMMA. The biochip has a commercially available size, i.e. about 2-5×2-5 mm, and has preferably square dimensions. Immobilization preferably occurs by covalent coupling of the FAKs to a functionalized coating of the biochip, such as, e.g., by coupling of lysine amino groups to an epoxysilane-functionalized glass support. A further function of the coating of the biochip is to prevent an unspecific attachment of the antigen to the surface of the biochip. An aminopropylsilane-, aldehyde- or poly-L-lysine-functionalized support could also be used instead of an epoxysilane-functionalized support.

The immobilization occurs in a spatially resolved manner and separately for each type of FAK in discrete areas (spots) on the biochip. The spot size ranges from 50 to 200 µm and the spot distance from 100 to 300 µm. Each type of FAK is available several times (replicates); there may be 2-24, preferably 4-12, and most preferred 6 positions. Furthermore, there are positions in which process controls take place, such as positive and negative controls.

In the following, the cartridge and the measurement procedure are described in more detail on the example of the sandwich ELISA with immobilized capture antibodies, this having to be understood as a possible exemplary embodiment and not as having a limiting effect. As regards the cartridge and the measurement process, many variations are possible which ensure a successful implementation of the method according to the invention.

For example, a small amount (e.g. 2 µl) of the sample with the antigen to be tested is added (using a standard laboratory pipette) to the biotest mixture reconstituted with the buffer containing Triton X. The resulting reaction batch (approx. 40 µl) is completely injected into the reaction space of the cartridge. The cartridge is then placed in the processing apparatus, and the analyzing process is started.

The antibody-antigen reaction then takes place in the sealed reaction space of the cartridge. In principle, this reaction works like a sandwich immunoassay, three bonds being established between four "proteins" (generally peptides). The capture antibody (FAK) is disposed in covalently bound form and in spotted fashion on the biochip; said antibody binds specifically to an epitope of the antigen (e.g. ricin). Then, there is the biotin-labeled detection antibody (DAK) which, in turn, binds specifically yet to another epitope of the antigen (AG). In order to visualize all of this, there is fluorescent dye-labeled streptavidin (SA) (e.g. as SA-DyLight647) which, in turn, forms a very stable bond to biotin and thus permits fluorescence detection at the point where the cascade (FAK)-(AG)-(DAK)-(SA) has come into being.

The standard ELISA, for example, proceeds such that a wash step is carried out between each specific binding reaction. At first, only the (AG) is added, and after an adequate period of time a wash step is carried out and any non-bound antigen is removed. Then, the (DAK) is added which binds specifically to the (AK)-(AG), this is followed by another wash step and the non-bound (DAKs) are removed. Next step: addition of the "visualizing protein". At the end of the standard ELISA process, a wash step is carried out again in order to minimize the background for the image recording. The selection of antibodies for such a detection method will thus, in addition to targeting specificity, mainly seek to ensure that the wash steps are survived as well as possible. The (FAK)-(AG) bond must withstand the wash procedure three times, the (AG)-(DAK) bond must withstand at least two wash steps, etc.

In the system according to the invention, all of the constituents are available at the same time! (AG) and (DAK) may bind to each other before the (AG) binds to the (FAK). During the incubation period, this means that these bonds (which are not covalent) are constantly formed and broken again. All of the constituents constantly form varying coalitions. However, given enough time, a thermodynamic equilibrium will establish and the system will move towards the energy minimum. The speed at which this happens (i.e. the required assay time) depends, to a substantial extent, on the temperature and the diffusion rates, but the result depends on the binding strengths since the stronger bonds are preferred in the equilibrium state. The viscosity and ionic strength of the buffer play a part here.

The temperature influence is such that at a more elevated temperature a sub-optimum bond is disrupted more easily/faster, i.e. the equilibrium is reached more rapidly. The diffusion rate depends inter alia on the size of the molecules; it takes in particular longer for a protein complex such as (AG)-(DAK) to diffuse towards the (FAK) than it would take the components to move there individually. The detergent (e.g.

Triton X) here has a certain influence since it contributes to keep the constituents somewhat apart. In addition, the viscosity of the solvent, of course, also has a direct influence on the diffusion.

In the system according to the invention, the bonds are never put to the test as a result of the lacking wash steps, what is decisive is the sufficiently fast production of the cascade (FAK)-(AG)-(DAK). Correspondingly, it is possible for antibodies which provide optimum results in the immunological standard method, e.g. ELISA method, to be unsuited for the system according to the invention and, vice versa, for antibodies which provide poor results in the immunological standard method (e.g. ELISA method) to be optimum for the system according to the invention.

In order to carry out the test in simple manner, a cartridge is necessary where after filling in the sample liquid different temperature profiles can be adjusted so that the corresponding biological reaction proceeds, followed by optical detection. This cartridge acts as a biological microreactor in which all biochemical reactions proceed in controlled fashion for the analysis of biological samples.

Two different kinds of cartridges I and II are described below, which are all functioning alternatives for the conduction of the immunological detection method.

Cartridge I is to be described first, it comprises:
a reaction space in which the biochip with the reaction areas (spots) applied thereon and including the known fixed capture molecules is disposed,
where appropriate, a filling device for introducing the sample liquid into the reaction space,
a temperature control device for adjusting different temperatures and their fast change in the reaction space,
a detection window serving for carrying out an optical detection of the spots on the biochip upon immunological reaction by means of an optical module.

The cartridge I contains an inlay having a biochip in the reaction space. M×N spots (reaction areas) including different biological pieces of information are arranged on the biochip. Known capture molecules are fixed on every spot; they only bind to one specific type of molecule each from the sample liquid to be investigated. The biological detection reaction is started after filling the sample liquid to be investigated into the reaction space. For this purpose, a defined temperature profile is run and the molecules are selectively bound to the spots on the biochip. The dye molecules which are chemically bound to these molecules can then be detected by means of an optical module and suitable optical fluorescence measurement methods.

The cartridge I and the measurement method can be described as follows in a preferred embodiment with reference to FIGS. 1-3:

A base body 1 produced by means of die casting, for example, contains recesses for the filling channel 7 with the check valve 8, the filling opening 9, the reaction space 5, the communication channel 4 between sample space 5 and compensation space 2 and an inspection window 3. The check valve 8 is inserted in the filling nozzle 9 where it is fixed (FIGS. 1, 3).

As an alternative, it is possible to provide a silicone gasket instead of the check valve, said gasket being adapted to be penetrated by a hollow needle for filling the sample space.

The biochip 6 (FIG. 2) contains a number of M–N reaction areas 6.1. In order to avoid optical back-reflections and undesired (fluorescence) radiation of the flex pc board, the biochip is optically opaque on its rear side and not fluorescent, e.g. coated with black chrome, for example. 6.2.

The biochip 6 is fixed on the flex pc board 10 and then the flex pc board is connected to the base plate 1. The flex pc board and the biochip are connected by means of an adhesive bond layer, such as a suitable adhesive tape (suited for biological reactions) or by means of a silicon adhesive. The flex pc board is then adjusted using the applied biochip to the base body where it is fixed to form the inlay. A permanent, temperature- and water-resistant connection can be realized by means of a biocompatible adhesive tape, by means of a silicone adhesive, by laser welding, by ultrasonic welding or other biocompatible adhesives, for example. In this connection, there is the possibility of extensively coating the entire flex pc board with the adhesive tape (or adhesive), of adhering the biochip over the heating structure of the flex pc board and then adjusting the base body relative to the biochip as well as fixing the flex pc board over the entire surface of the base body.

A second possibility of connecting flex pc board, biochip and base body consists of the selective laminar adhesion of the biochip with the flex pc board (adhesive only underneath the biochip) and the subsequent fixation of the basic body only outside the reaction space. The heat transfer from the heating structure 10.3 in the flex pc board to the reaction space is more efficient with this type of adhesion.

The thus pre-assembled inlay unit which consists of base plate, biochip, flex pc board and check valve is pressed into a cartridge for simpler handling and stabilization.

The filling operation of cartridge I takes place as follows:
The sample liquid is injected into the reaction space through the check valve 8 or through the silicone gasket via the filling channel 7. The sample liquid initially fills the reaction space 5 and then flows into the compensation channel 4. During the filling operation, an excess pressure forms in the inlay system and the air in the compensation space is compressed. The filling level can be monitored through a control window in the compensation channel 4. Since the volumes of the filling channel 7, the reaction space 5 and the compensation channel 4 are known, it is possible to carry out the filling operation with a constant liquid volume, even without inspection of the optical window.

The pressure-tight sealing with a check valve 8 or the silicone gasket produces an excess pressure in the reaction space when the cartridge is filled. The air in the compensation volume is compressed. The excess pressure can be selectively adjusted by varying the volumes of the reaction and compensation spaces. When the volumes of the reaction and compensation spaces are equal, the internal pressure doubles during filling. The thermal expansion of the sample liquid results in an escape into the compensation channel 4. During cooling, the sample liquid retreats again. The pressure differences at $T_{max}$ and $T_{min}$ (in the cold and hot states) are only minimal since the air in the compensation space is compressed. The volume of the compensation space is markedly greater than the volume increase in the sample liquid during heating.

A stabilizing disk inserted in the cartridge can minimize an expansion of the resilient flex pc board 10 during the filling operation without losing the capability of resiliently pressing the biochip 6 against the detection surface.

A pressure increase by 1 bar in the cartridge has the advantage that the boiling point of the sample liquid increases. The formation of air bubbles in the reaction space is thus minimized and the mixing of the reaction components is facilitated. The run of a temperature-controlled biological detection reaction requires the adjustment of precise temperatures of the sample liquid in the reaction space, i.e. a reaction space whose temperature can be adjusted. Here, temperatures between 20° C. and 50° C., preferably between 30° C. and 40°

C., most preferably between 35° C. and 39° C., for example, are targeted when an ELISA is carried out. The temperature distribution of the sample liquid must be homogeneous in the reaction space and temperature changes (heating, cooling) are to be carried out rapidly.

When it comes to the optimum conduction of the immunoassay, the temperature is an important component. In the broadest sense, it has to be regarded as the driving force which supplies the necessary activation energies. By means of a temperature change showing only a small temperature difference, it is possible to generate in the reaction space a convection which accelerates the diffusion rate of the molecules and this has a positive effect on the reaction time. The batch is advantageously controlled with cycling temperature, changes for up to 30 minutes between 30° C. and 40° C. alternating with holding times for 30 seconds each followed by recording an image at 37° C.

A heating structure 10.3 which when a current is applied acts as a heater as a result of the ohmic resistance is disposed on the flex pc board 10 of the cartridge I. Thus, the sample liquid is heated in the reaction space to the necessary temperature T. The heating structure can simultaneously be used as a temperature detector by using the characteristic resistance curve R(T) for determining the temperature.

The pc board having the integrated heating tracks causes local temperature fluctuations. Hot spots are disposed directly above the heating structures. A preferably applied temperature homogenization layer on the pc board effects a homogenization of the temperature distribution on the top side of the pc board.

A heater integrated into the pc board has a low thermal capacity of its own. Thus, greater heating rates $\Box T(t)$ of the sample liquid can be realized in the reaction space.

The sample liquid is cooled in the reaction space by means of either air, cooled air or fitted cooling elements.

The temperature control in the reaction space is described in more detail in the applications WO/2008/000767 A2 (PCT/EP2007/056420) and WO/2008/000770 A2 (PCT/EP2007/056430), to which reference is made herein and the contents of said applications are introduced here by reference.

When it comes to the image recording, the flex pc board 10 is elastically deformed by forcing-in the tappet 12 when the cartridge I is used after carrying out the immunoassay so that the adhered biochip 6 is pressed against the detection surface (FIG. 3). In order to overcome the air pressure in the compensation space, a force $F_0$ must be applied. With an area of about 0.5 cm$^2$, only about 5 N is necessary to build up a pressure of 1 bar. In addition, a certain force $F_1$ has to be applied to deform the elastic flex pc board with the attached biochip 6 by means of a tappet 12 so as to press the biochip uniformly against the detection surface. The sum of the forces $F_0+F_1$ shall not be above 30 N.

The above mentioned "tappet movement" is described in DE 10 2004 022 263 A1 to displace the liquid supernatant by mechanical means so that there are no (or only some few) dye molecules between the biochip and the detection surface. The reaction space is, in this connection, designed such that a tappet presses the biochip against a planar detection surface 14 so as to displace the intermediate sample liquid, i.e. the liquid supernatant.

During the tappet movement, the excess sample liquid containing dye molecules, i.e. the liquid supernatant, between biochip and detection surface is displaced. It then fills the compensation channel and the compensation space. The illumination unit of the optical module 27 only stimulates the dye molecules bound on the biochip to emit fluorescence. After the tappet movement, the detection unit of the optical module 27 only detects the fluorescence light of the dye molecules bound on the biochip.

The biochip is illuminated via a suitable light source which is adapted to the employed dye in the sample solution. Laser and LED are preferably suited as a light source. A function of the optical module is the realization of the homogeneous biochip illumination. It can be realized with a suitable optical module. By means of a rectangular aperture which is mechanically mounted on the base body above the reaction space or integrated thereinto and has geometric dimensions that are somewhat smaller than the biochip, the optical fluorescence excitation of the dye is prevented in the reaction space next to the biochip.

During the injection molding of a transparent base body, this aperture can be introduced as an optically absorbing aperture or, during the injection molding of a non-transparent base body, as a transparent optical aperture. The aperture can also be fixed subsequently to the optical observation window (detection surface). The transmission of the aperture layer is to be less than $10^{-2}$.

The above mentioned optical module is described in more detail in the application PCT/EP2007/054823, to which reference is made herein, and the content of this application is integrated hereinto by reference.

When it comes to the use of cartridge I there is, contrary to the device in DE 10 2004 022 263 A1, where the sample liquid is irreversibly displaced out of the reaction space by the tappet movement before the image is recorded, the possibility in the cartridge used according to the invention to carry on the immunoassay after the image is taken. When the tappet is retreated, the flex pc board retreats as a result of the excess pressure in the reaction space and the sample liquid flows from the compensation channel back into the reaction space, also between the biochip and the cover glass. Thus, the ELISA can be continued even after the detection as made. A real-time detection is in particular possible.

The cartridge II which is possible alternatively to the above described cartridge I preferably comprises:
- a reaction space and a biochip arranged within the reaction space,
- a filler neck which is connected with the reaction space in communicating fashion, and
- a compensation space which is connected with the reaction space in communicating fashion, the reaction space, the compensation space and all lines connected therewith forming a space confined except at the filler neck, the filler neck forming a free passage from outside the cartridge to the reaction space and a tappet being provided which is accommodated in the filler neck in positive and tight fashion so as to displace fluid from the filler neck towards the reaction space when it is forced inwards via a certain path.

The following advantages are obtained by this:

1. Since the filler neck is open, the sample solution can simply be filled in by means of a standard pipette, for example. No syringe is required to penetrate a membrane. No pressure has to be built up to penetrate a valve. During filling, there is no force and no counter pressure which have to be overcome to introduce the sample into the cartridge. The filling step is carried out without pressure. There is no danger that part of the samples is spilt during the filling operation.

2. The sample solution is pressurized when the plug is forced in. As a result, the boiling point increases. Due to this, no gas bubbles which might impair the measurements form in the sample solution even if the latter is heated to temperatures in the range of about 100° C.

3. The air in the compensation space has an effect on the sample solution the same as that of an elastic spring member which permits a further displacement of sample solution, the reset force exerted on the sample solution by the air being small. Thus, the force which has to be applied to a transparent flexible film which confines a side of the reaction space to displace the sample solution is small as compared to the conventional reaction spaces having membranes.

4. A danger of contamination is ruled out for the environment by the tight closure of the cartridge with the plug.

The open filler neck is connected with the reaction space, a level indicator and the compensation space via lines in communicating fashion so that before the filling operation ambient pressure or normal pressure prevails in all cavities of the cartridge II. When the sample liquid is filled in, the filler neck fills. When the plug is forced inwards, the air in the cartridge is compressed. Since sample space, compensation space and filler neck communicate, the pressure in the entire vessel system is simultaneously compensated. The volumes are here dimensioned such that the reaction space is fully filled with sample liquid and an internal excess pressure of 0.3-0.5 bar and preferably about 0.4 bar is produced. The pressure is minimally changed via a movement of the plug and causes a movement of the liquid in the sample space, which effects mixing.

The cartridge II has an open filler neck. As a result, it is possible to fill in the sample solution by means of a pipette. It is not necessary to use a hollow needle by means of which, as is the case of conventional devices of this type, a gasket is penetrated or to force the sample liquid under pressure through a valve.

In an embodiment of the cartridge II, the cartridge area opposite the biochip is designed as a transparent film. The flexible transparent film serves as a window for the optical measurements of the sample solution. In connection with this design, it is advantageous for the biochip per se not have to be moved in the reaction space.

In an embodiment of the cartridge II, one side of the reaction space is confined by a pc board. The biochip is arranged directly on the pc board. Heating/measurement structures may be integrated into the pc board. Such a pc board serves for heating and measuring the sample solution.

The cartridge II is preferably made of COC (cycloolefin copolymer). The latter is an inert plastics material which does not require an additional passivation of surfaces to carry out temperature-controlled biological reactions in the reaction space.

The transparent plastics film can be provided with an adhesion or adhesive layer on its side facing the biochip. Said layer can be activated when it contacts the sample solution. When the plastics film is forced against the biochip, it adheres to the biochip so as to prevent penetration of sample solution between biochip and plastics film. This adhesion layer is preferably provided in the area of the film which does not come into contact with the area containing the spots of the biochip. The adhesion layer is thus arranged circumferentially around the active area of the biochip.

The cartridge II is described in more detail below in a preferred embodiment by means of FIGS. 4-12:

The cartridge 101 has an elongate housing 102 which has approximately the shape of a basin or trough and is made of plastics by means of injection molding, for example. The housing 102 comprises a base wall 103 and a circumferential side wall 104 having two longitudinal sides 105 and two front sides 106. The side of the housing 102 at which the side wall 104 is arranged is referred to as the inner side 107.

A pc board 108 is mounted on the housing 102 on the side, facing away from the side walls 104, of the base wall 103. This side of the housing 102 is referred to as the outer side 109.

A tubular section extending in the longitudinal direction is formed as a filler neck 110 at one of the front sides 106 of the cartridge 101. The filler neck 110 has a filling section 111 and a compaction section 112. The compaction section 112 is a cylindrical section 116 having a circular cross-section which changes into a funnel-shaped section 117 at the end of which a filling opening 118 is formed. The filling opening 118 is connected with a reaction space 122 via a filling line section 120. In the cylindrical section 116 of the compaction section 112, a level indicator 119 is provided. The filling section 111 has a clear diameter greater than that of the compaction section 112. A chamfer 113 is provided as a transition between the filling section 111 and the compaction section 112. This chamfered section 112 has a sealing point 114 approximately in the center from which a plug 115 tightly seals the filler neck 110.

A compensation line section 123 is connected to the tip, oriented towards the filler neck 110, of the rhombic through opening 121 and opens into a tip of a compensation space 124 having the shape of a half-cone.

A through bore 125 is adjacent to the tip of the rhombic through opening 121. In connection with a semi-sphere 126 made of transparent plastics, this through bore 125 forms a level indicator 127.

The reaction space 122 or the through opening 121 is confined by a flexible transparent film 128 on the inner side 107 of the base wall 103. The film 128 is adhered to the base wall 103. The film 128 is preferably made of a perfluoroethylenepropylene copolymer (FEP) or another suitable plastics material. The flexible transparent film 128 serves as a window for the optical measurements of the sample solution. A circumferential gasket 129 is arranged on the film 128 in the area around the through opening 121.

In the area of the rhombic through opening 121 or the reaction space 122, the pc board 108 forms a confining wall thereof. In the area of the filling line section 120, the compensation line section 123, the level indicator 127 and the compensation space 124, the pc board 108 seals with said recesses in a tight fashion such that they are confined downwardly and form a continuous communicating, self-contained channel structure.

The pc board 108 contains contact surfaces, a digital memory medium (e.g. an EEPROM) and an internal heating/measuring structure 132 which are all explained in more detail below. In place of the pc board 108 it is also possible to provide a plate made of a well heat-conducting material having a micro-Peltier element provided thereon for heating and cooling.

In approximately the middle in the through recess, a biochip 130 is arranged on the pc board 108. The biochip 130 has a height of about 0.7 mm and a number of M×N spots. In order to avoid optical back-reflections and undesired fluorescent radiation from the pc board 108, the biochip 130 is optically opaque on its rear side and does not fluoresce, e.g. it is coated with black chrome.

The reaction space 122 is confined between the pc board 108 and the film 128 and by the edge of the rhombic through opening 121. The pc board 108 is provided with the heating/measuring structure to heat the biochip 130 to a predetermined temperature and measure said temperature. The film 128 serves as an inspection window for an optical detection device which can optically sample spots on the biochip 130 through the film 128. Since the film 128 can be made in flexible fashion, it can be attached to the surface of the biochips 130 for sampling the same.

In order to close the filler neck 110 and to generate an excess pressure in the reaction space 122, a plug 115 is provided. The plug is preferably made of a thermoplastic elastomer (TPE). The plug 115 is cylindrical and has a circular cross-section. The outer diameter of the plug 115 is made such that it can be received in almost clearance-free fashion in the compaction section 112 of the filler neck 110. The cylindrical compaction section 112 of the filler neck 110 and the plug 115 form kind of a cylinder-piston system. The plug 115 is provided with a sealing ring 131 made of a material preferably the same as that of the plug. The plug 115 can also be provided with a circumferential groove in which a sealing ring 131 is arranged. The plug 115 seals the cavities of the cartridge 101 in fluid-tight fashion after about one third of its length has been inserted in the filler neck 110.

In the area of the tip, oriented towards the compensation space 124, of the reaction space 122, a circular centering pin 144 is vertically attached. The centering pin 144 serves for centering when the sampling chamber is attached.

The filling and compensation line sections 120, 123 are as short as possible and formed with a smallest possible cross-section so as to keep the dead volume small and the necessary excess of sample liquid small. Nevertheless, the line sections 120, 123 are guided about the reaction space 122 so as to fill the reaction space 122 from below during the filling operation in which the filler neck 110 is arranged on the top. This ensures the bubble-free filling of the reaction space 122. During the operation, the filler neck 110 is arranged at the bottom and the compensation chamber 124 is arranged at the top so that sample liquid can reversibly be displaced into the compensation space 124, the air bubble being disposed in the compensation space 124 always above the sample liquid.

The run of a temperature-controlled biological detection reaction requires the adjustment of precise temperatures of the sample liquid in the reaction space. In this connection, temperatures between 20° C. and 50° C., preferably between 30 and 40° C., most preferably between 35° C. and 39° C., for example, are targeted when an ELISA is carried out. The temperature distribution of the sample liquid must be homogeneous in the reaction space and temperature changes (heating, cooling) shall take place rapidly. For an optimum conduction of an immunoassay, the temperature is an important component. In the broadest sense, it is the driving force which supplies the necessary activation energies. When changing the temperature with only a small temperature difference, it is possible to produce convection in the reaction space, thus accelerating the diffusion rate of the molecules, which has a positive effect on the reaction time. The batch is advantageously controlled with cycling temperature, changes between 30° C. and 40° C. for up to 30 minutes alternating with holding times of 30 seconds each, and then an image is produced at 37° C.

A heating/measuring structure 132 is disposed on the pc board 108 which when the current is applied acts as a heater as a result of the ohmic resistance. The sample liquid in the reaction space 122 is thus heated to the necessary temperature T. The heating/measuring structure 132 can simultaneously be used as a temperature detector by using the characteristic resistance curve R(T) for determining the temperature.

The pc board 108 can be provided with a temperature homogenization layer which effects a homogenization of the temperature distribution on the top side of the pc board 108.

The electric control of the heating/measuring structure 132 is described in detail in WO 2008/064865 A2. Reference is made to this document or the control of the heating/measuring structure 132.

The pc board 108 has pc board tracks 137 and corresponding contact points 138, 139 for connecting an electric semiconductor memory. This semiconductor memory serves for storing calibrating data for the heating device and the data of the biological experiments which are to be carried out with the biochip of the cartridge. This data is thus stored in confusion-proof fashion.

The coupling of the cartridge 101 into a device for the immunological detection of biological samples is described below. This device comprises a sampling chamber 140, a detection device 149 and a compressed-air supply source 150.

The tubular sampling chamber 140 is attached with an open sample side 141 on the film 128 confining the reaction space 122 or on the gasket 129 arranged thereon.

The diameter of the tube 140 on the sample side 141 corresponds to the diameter of the gasket 129 arranged on the film 128. The sample side 141 is confined at its front by a sharp-edged circumferential blade 142. This blade 142 is made such that when the sampling chamber 140 is attached on the cartridge 101 it penetrates the gasket 129 of the cartridge 101 so as to establish a pressure-tight connection.

Recesses 143 are provided on the sample side 141 of tube 140 to accommodate the centering pin 144 and both stops 145 of the cartridge 101. In this way, the sampling chamber 140 is positioned accurately on the cartridge 101 or its gasket 129 and above the reaction space 122. The accurate abutting pressure is adjusted by stops 145 with which the sampling chamber 140 abuts in pressure-tight fashion against the cartridge 101.

A compressed-air line 148 is connected in approximately the center of the tube 140 and is connected with a compressed-air supply source 150. Compressed air can be applied to the sampling chamber 140 via the compressed-air supply source 150 and the compressed-air line 148 in the area between the lenses 147 and the cartridge 101. In this way, the film 128 is abutted against the biochip 130 in laminar fashion.

A detection device 149 for sampling the biochip 130 is arranged behind the two lenses 147.

The detection device 149 for reading out the biochip 130 is described in detail in WO 2007/135 091 A2 to which reference is herewith made. The optical detection device 149 comprises an LED having a plastics optics cast thereon (preferably Lambert LED), an LED optics, an illumination optics, an excitation filter, a dichroitic mirror, an NA aperture, an emission filter, a read-out optics and a camera.

A single high-performance LED having a high performance optical density and an LED optics having a high numerical aperture (NA) are preferably used as a light source. High-performance light-emitting diodes are light-emitting diodes having a luminous flux of at least 35 lm. Light-emitting diodes are preferably used with a luminous flux of at least 40 lm, at least 50 lm or at least 100 lm. In the present embodiment, the light-emitting diode Luxeon Star (red, 1 W electric power input, 42 lm luminous flux) is used.

An advantage of an LED for the illumination of biochips is also the variability of the wavelength. LEDS are available over the entire visible spectrum with high efficiency.

As to the typical dyes to be detected in the spots on the biochip, it is possible to use a spectrally well adapted LED as a light source.

For example:

Dye Cy5 absorption maximum at 649 nm
excitation with LED LUXEON LD3 (color red, maximum at 630 nm)
Dye Cy3 absorption maximum at 514 nm
excitation with LED LUXEON LM3 (color green, maximum at 530 nm)
Dye Alexa Fluor 532 absorption maximum at 532
excitation with LED LUXEON LM3 (color green, maximum at 530 nm)

The selection of an LED is made for a wavelength range $\Delta\lambda_E$ which is required for fluorescence measurements (e.g. for the dyes Cy5, Cy3, Alexa, . . . ).

The camera has a planar CCD element as a detector so that a rectangular, in particular square, image can be detected. The camera is designed such that exposure times of up to 20 seconds can be made with it. The longer the exposure time, the weaker fluorescence signals can be detected. The strength of the fluorescence signals strongly depends on the number of immune reactions carried out on the biochip 130. These relatively long exposure times also represent an advantage in the light of conventional scanners which sample the individual spots line by line since the exposure time cannot be freely varied by this method.

The use of the cartridge II for carrying out and investigating biological samples with temperature-controlled biological reactions is described below.

The sampling chamber 140 is attached with its sample side 141 on the film of the cartridge 101. Here, the recesses 143 of the sampling chamber 140 mesh with the centering pin 144 and the two stops 145 so as to position the sampling chamber 140 and confining the abutment pressure applied to the gasket 129. The blade 142 here penetrates the gasket 129 and ensures a pressure-tight connection.

The sampling chamber is filled with air via the compressed-air line. In this way an excess pressure between 2 bar and 4 bar is generated in the space sealed between the optics 146 and the transparent film 128. The transparent film 128 attaches to the biochip 130 as a result of the excess pressure and displaces the fluorescence supernatant of the sample liquid above the biochip 130. The fluorescence in the rest of the sample chamber is screened off. A fluorescence image of the biochip 130 can thus be recorded.

A mixing (compulsory convection) of the sample has a positive effect on the reaction rate of the hybridization/incubation and therefore the incubation time is shortened and higher signal intensities are possible. As a result, such a compulsory convection cannot only be achieved by varying the temperature but also by varying the excess pressure externally applied to the film.

The "window" film 128 is mechanically loaded, in particular during heating, by the internal excess pressure of the cartridge 101 of 0.4 bar and would deform plastically. This load can be neutralized by an external excess pressure of also 0.4 bar. This is of advantage e.g. during the immunological reaction where the film is considerably loaded thermally.

In connection with the above described device it is advantageous that large-area surface unevenness is left on the biochip 130—this being different with respect to cover glasses known from the prior art—without having an influence on the fluorescence signal.

The optical quality of the film 128 has only a minor influence on the assessability of the fluorescence signals due to its minor thickness and the vicinity of the film 128 to the biochip 130.

The attachment of the sheet 128 to the biochip 130 is reversible and thus a real-time detection is possible.

When the cartridge I or II is used, the spots on the biochip can, in principle, be detected at a time of the biological reaction.

The above described embodiments of the cartridge I or II are to be understood as advantageous embodiments and by no means as limitations for the conduction of the immunoassay. Functional modifications are within the skill of the person skilled in the art and shall not be ruled out.

Irrespective of the cartridge (I or II) which is used, the read-out and writing-in of data is made on the basis of the same principle:

All pieces of information on the cartridge, including the biochip, must be read out by the biochip reader. When it comes to the targeting of accurate temperature, the data of the heater is required on the pc board. The information on the reaction areas (spots) applied on the biochip, ID numbers, exposure times for the image record, etc., must be read out by the reader to control the temperature-controlled biological reaction and enable a recording and archiving.

The necessary information can be attached as a dot code or as a bar code to the cartridge. For reading out these codes, a dot code reader (or bar code reader) is required. The use of writable and readable manipulation-proof storage media which are advantageously integrated on the pc board is more flexible.

Along with the contact surfaces of the heating structure, it is also possible to contact an electrically programmable non-volatile memory on the pc board. As a result, information can be stored digitally and retrieved at any time. The storable data amount is here markedly greater than in the case of attached bar or dot codes.

The resulting information is processed by a suitable software, the spatial arrangement of the FAK spots (array layout) being already deposited in the software via the software.

In the case of a contacted, electrically programmable non-volatile memory, it is also possible to store information during the immune response when the biochip is read out. In addition, the data can be stored in manipulation-proof fashion. After the processing step, the cartridge can also be marked as "processed".

In summary, the advantages of the procedure according to the invention are:

Highly integrated system having a minimized number of manual steps

No wash steps therefore optimum correlation of binding partner amount and signal Multiplexing detection system:
  A cartridge type for the detection of several substances
  Simultaneous detection of several substances or several features on a substance in a "single" reaction Possible influences on the assay run very high, as a result of time/temperature control. Therefore, simple optimization of the parameters is possible for different detections and:

Simple conversion of new detections on the system platform. Only the corresponding binding partners have to be used.

There are several system-related special features which distinguish the described system according to the invention from known methods:

More than 2 binding partners

Without washing

All biochemical reactions between the involved binding partners, which are carried out one after the other in the standard sandwich ELISA, for example, (with wash steps in between) take place in the one-step immunoassay simultaneously/together. The driving force is here the diffusion. The diffusion rate is determined by temperature, viscosity and molecule size, for example; convection can accelerate the diffusion. In the one-step sandwich ELISA according to the invention for an antigen detection these are the following reactions, for example:

Capture antibody-antigen

Antigen—biotinylated detection antibody

Biotinylated detection antibody—streptavidin-Cy5

The detection cannot be made until all reactions have taken place.

In order for the binding partners not to compete with one another in the various reactions, the reaction conditions have to be adjusted in optimum fashion. Otherwise, the reliable immunological detection would be prevented.

These reaction conditions to be adjusted are in particular:

1. Biochip/Microarray

Fixation of the protein spots using a stabilizer (most preferably: trehalose) to obtain the tertiary structure of the proteins; in addition increase in the durability.

Drying of the protein biochips treated with trehalose and dissolution during the one-step immunoreaction by the detergent contained in the biomix (most preferably: triton X)

No blocking of the biochip after spotting, the reaction of the functional epoxy groups between the spots takes place during the reaction by the biomix buffer.

2. Biotest Mixture

Composition of the biotest mixture, in particular triton X, as a detergent and its concentration (viscosity of the biotest mixture influences the diffusion)

Ionic strength of the biotest mixture buffer

Concentration of the detection antibodies

3. Processing Parameters

Temperature (influences the diffusion): best temperature range is 37° C.±2° C.

Convection in the sample space can accelerate diffusion and thus accelerate the reaction so as to considerably reduce the processing time. The convection is achieved by cycling the temperature, for example, e.g. change between 32° C. and 40° C. every 30 seconds each or by minimum pressure changes in the sample space Sample volume influences the diffusion, in particular the diffusion times 4. Cartridge Detection: displacement of the fluorescent liquid replaces the wash step!

As a result of the mechanical displacement, the background becomes lower and more uniform during the detection than can be achieved by the wash steps. This results in a high signal-to-background ratio and thus in a more sensitive measurement method which also shows low assay variances. The reason for this is that the specific bonds to the substrate are not impaired by washing and thus there is no signal loss resulting from washing away. In addition, the background remains weak and simultaneously uniform as a result of the "non-washing". This is a huge advantage which is more marked in immunological detections than in DNA detections, for example.

BRIEF DESCRIPTION OF THE FIGURES

The invention is further described by means of the illustrations (figures) wherein:

FIG. 9 shows a filling procedure of cartridge II with the plug forced in, FIG. 13 shows the development of a multiplex sandwich assay, FIG. 14 shows an array layout, FIG. 15 shows designations of the antibodies, FIG. 16 shows a scan image after spotting, FIG. 17 shows a reaction mechanism of the epoxy linkage, FIG. 20 shows the alignment of the array, FIG. 22 shows the time kinetics of the ricin detection (single plex), FIG. 23 shows the "4-plex assay"

Figure 24:
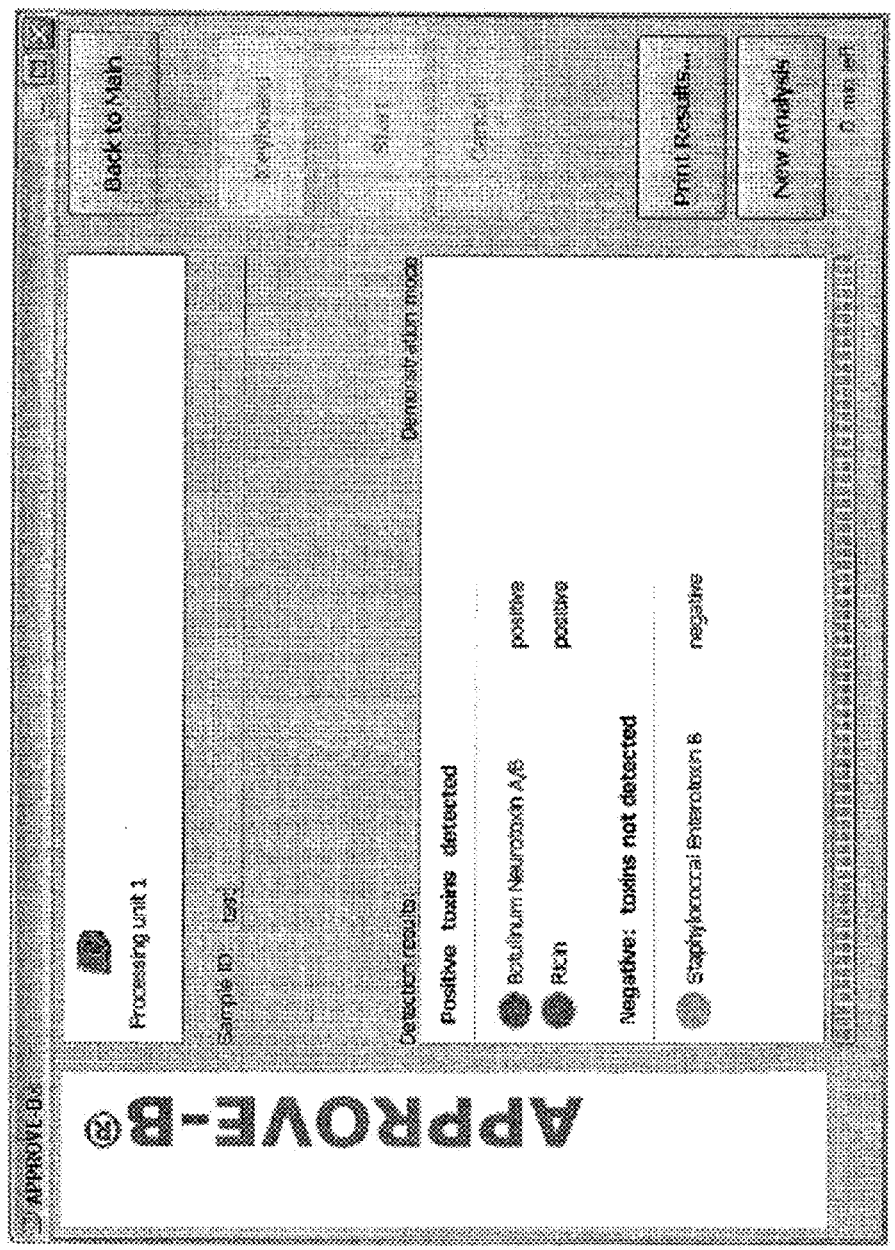
Figure 25:
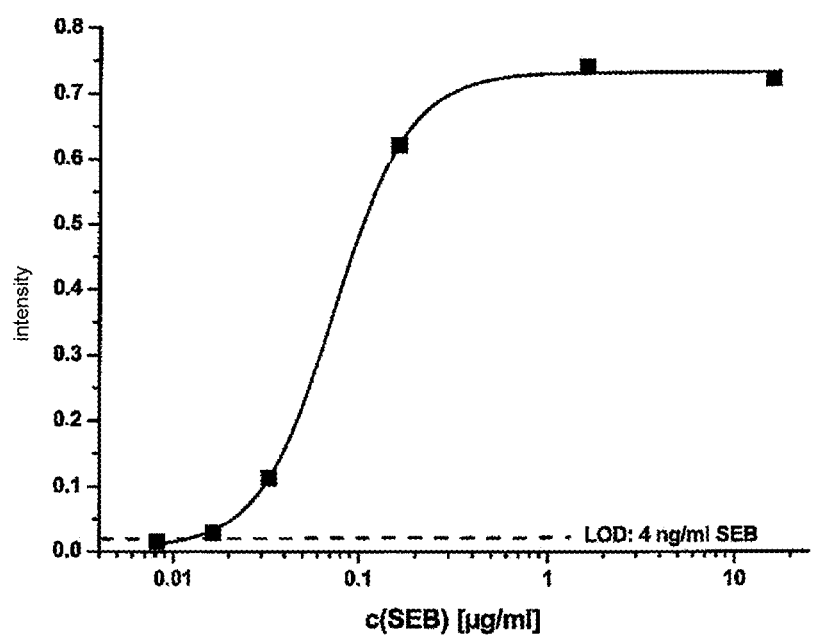

spotting of various capture antibodies (monoclonal and polyclonal) per toxin a detection antibody per toxin (mAb)

the simultaneous detection of ricin, BoNT/A, BoNT/B and SEB within 30 minutes the detection of purified toxins or Crude preparations/culture supernatants possible, FIG. 24 shows the presentation of the final results after automatic evaluation by the software: positive detection for BONT A/B and ricin, negative detection for SEB, FIG. 25 shows the LOD determination for SEB toxin.

The invention is further described by means of the below exemplary embodiments which are to represent an exemplary implementation of the invention but should not be interpreted as a limitation of the scope of protection.

DETAILED DESCRIPTION OF THE INVENTION

Example 1

Toxin Detection

The simultaneous detection of three toxins that can be used as bioweapons is possible with the toxin assay. The toxins are ricin, staphylococcus enterotoxin B (SEB) and the botulism toxins A and B (BoNT A/B). In their active form, the toxins can be present as a crude extract or in purified form, mineral water being established as a sample matrix.

1. Biochip

The glass support for the biochip consists of a float glass (SCHOTT Borofloat 33, thickness of 0.7 mm). It is coated with an antireflective coating on the rear side. The reflectivity is minimized at the excitation wavelength (630 nm).

Figure 1:
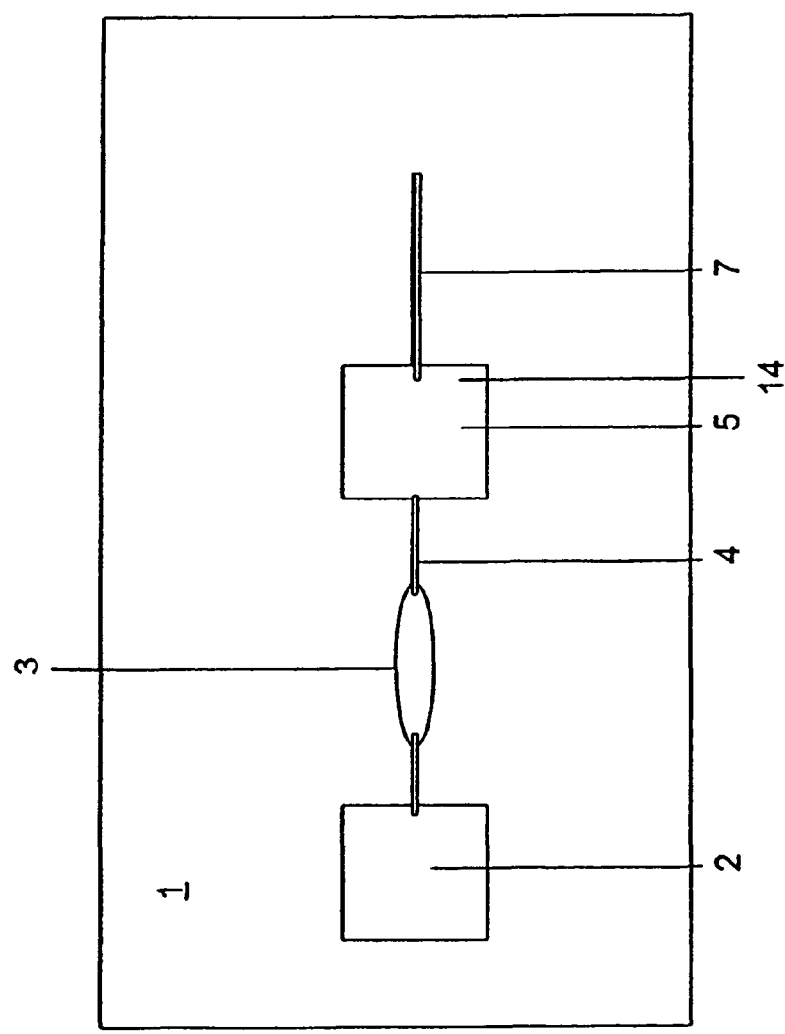
FIG. 1 shows the base body of the cartridge I
Figure 2:
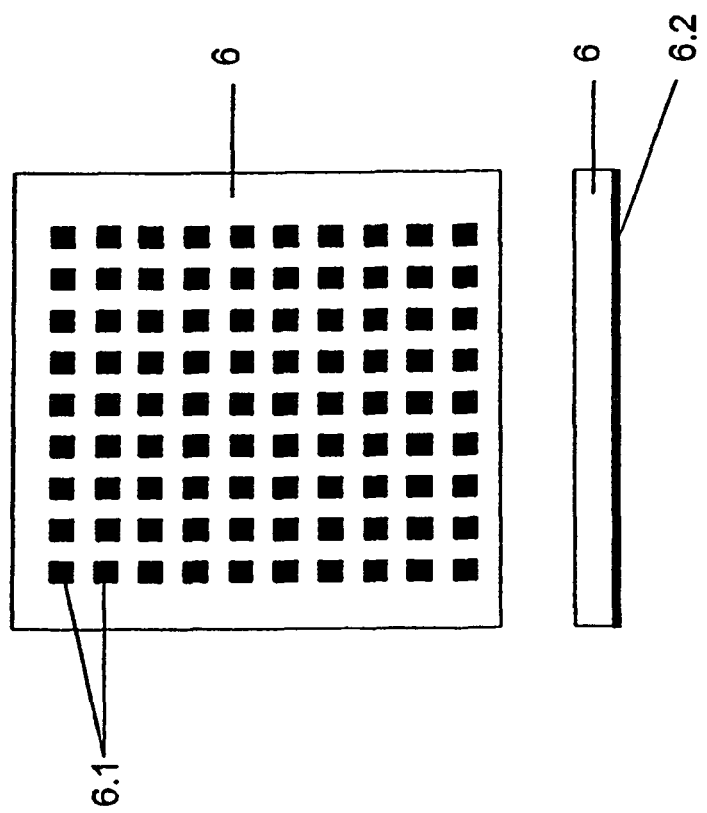
FIG. 2 shows a design of the reaction areas (spots) on the biochip with optically impermeable and non-fluorescent rear side
Figure 3:
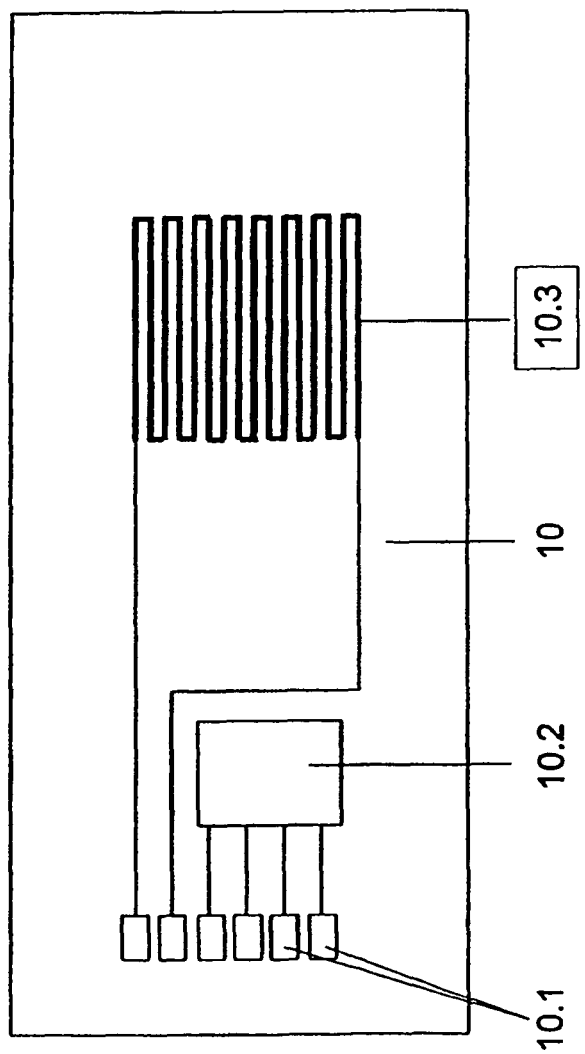
FIG. 3 shows an arrangement of the inlay with the associated optical module
Figure 4:
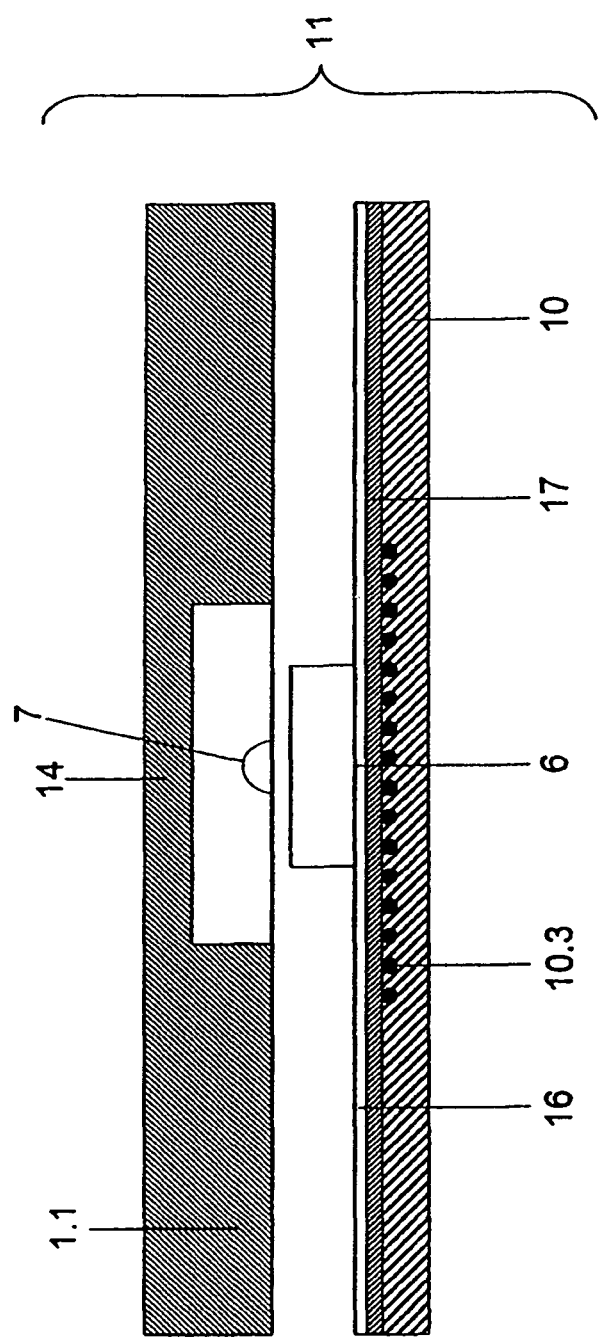
FIG. 4 shows a perspective view of a housing of cartridge II.
Figure 5:
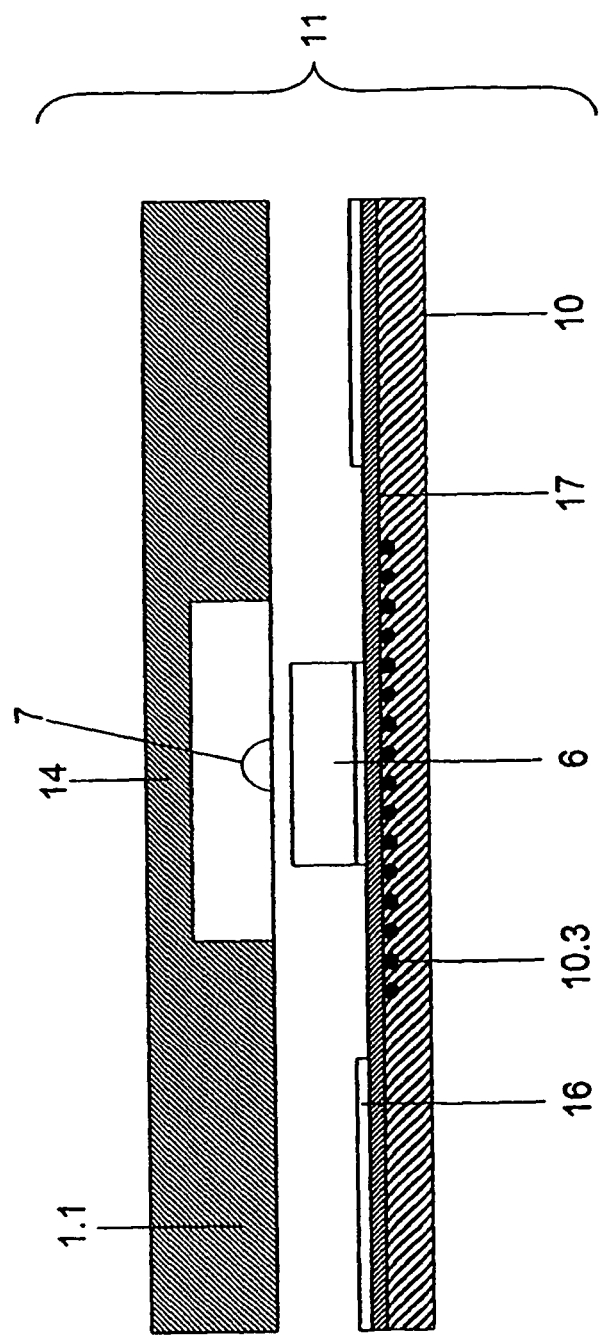
FIG. 5 shows the view of the housing from FIG. 4 in a side view in partial section together with a plug.
Figure 6:
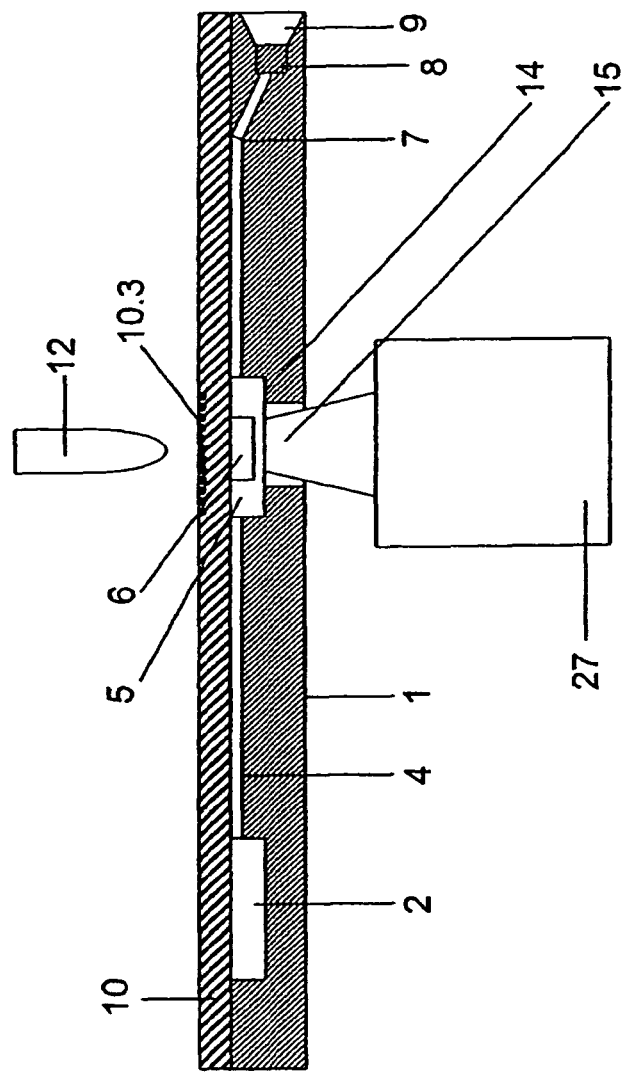
FIG. 6 shows a longitudinal section through an area of cartridge II.
Figure 7:
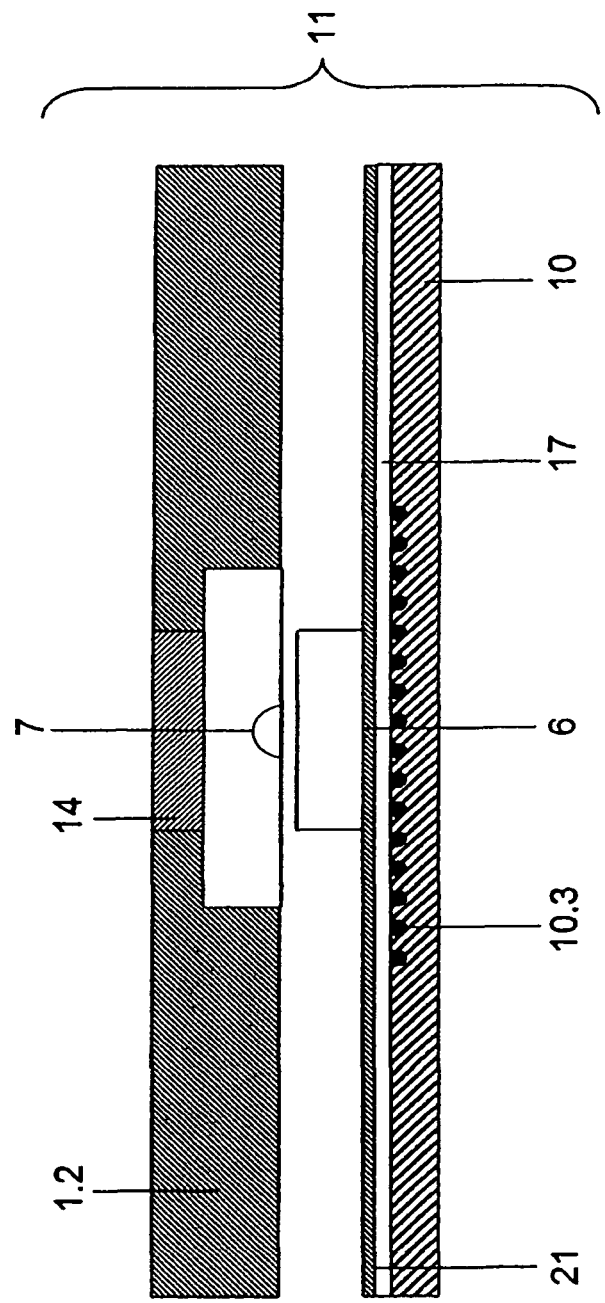
FIG. 7 shows a section through cartridge II and a sampling chamber.
Figure 8:
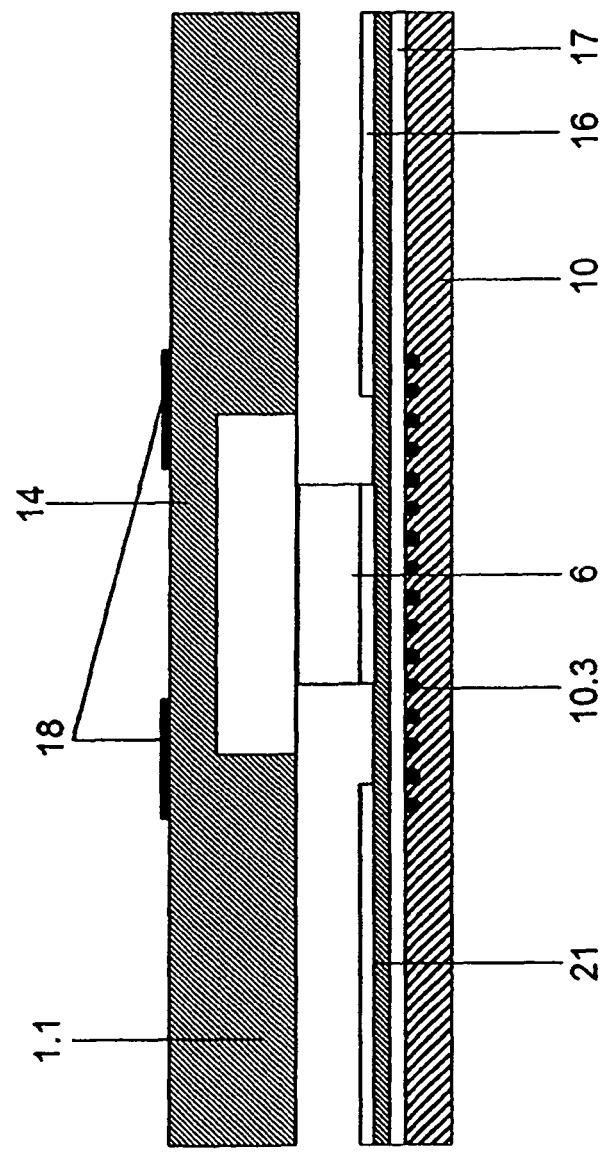
FIG. 8 shows a filling procedure of cartridge II with the plug not attached.
Figure 9:
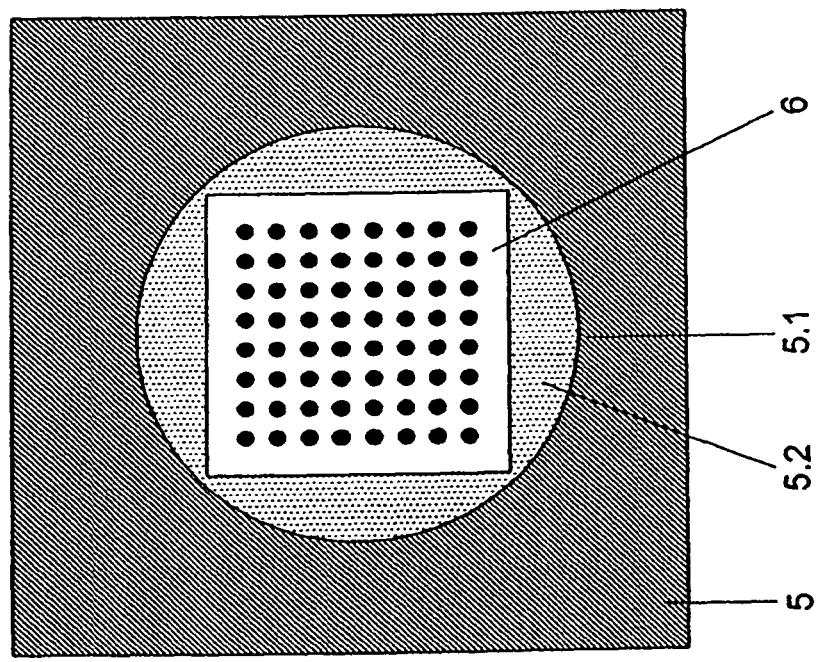
Figure 10:
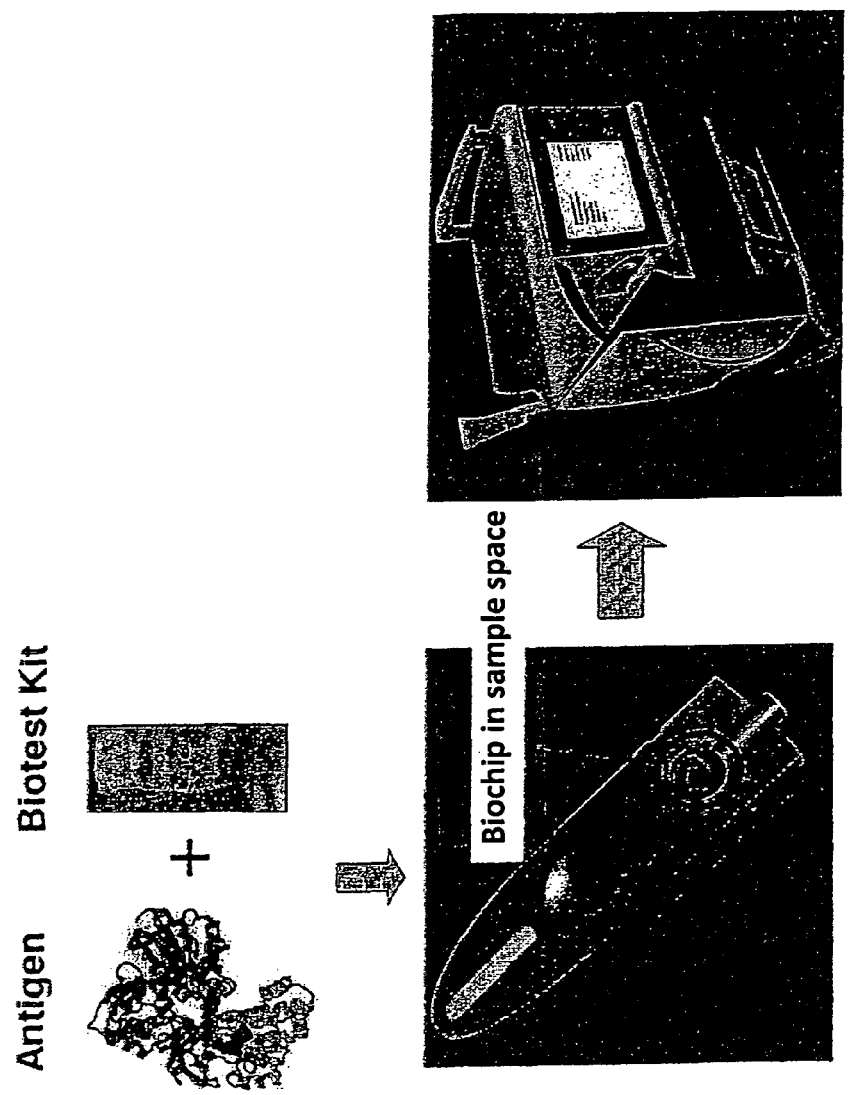
FIG. 10 shows the pc board of cartridge II with a heating/measuring structure.
Figure 11:
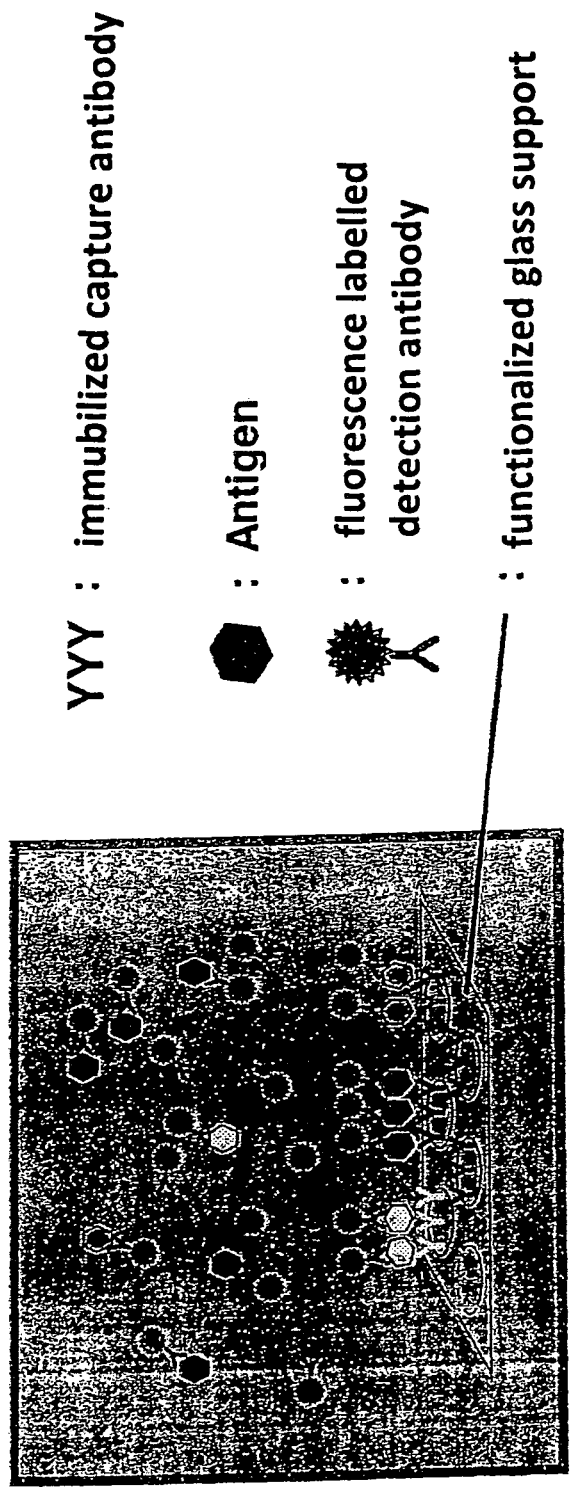
FIG. 11 shows the sampling chamber of FIG. 7 and a compressed-air supply source attached thereto in a sectional view.
Figure 12:
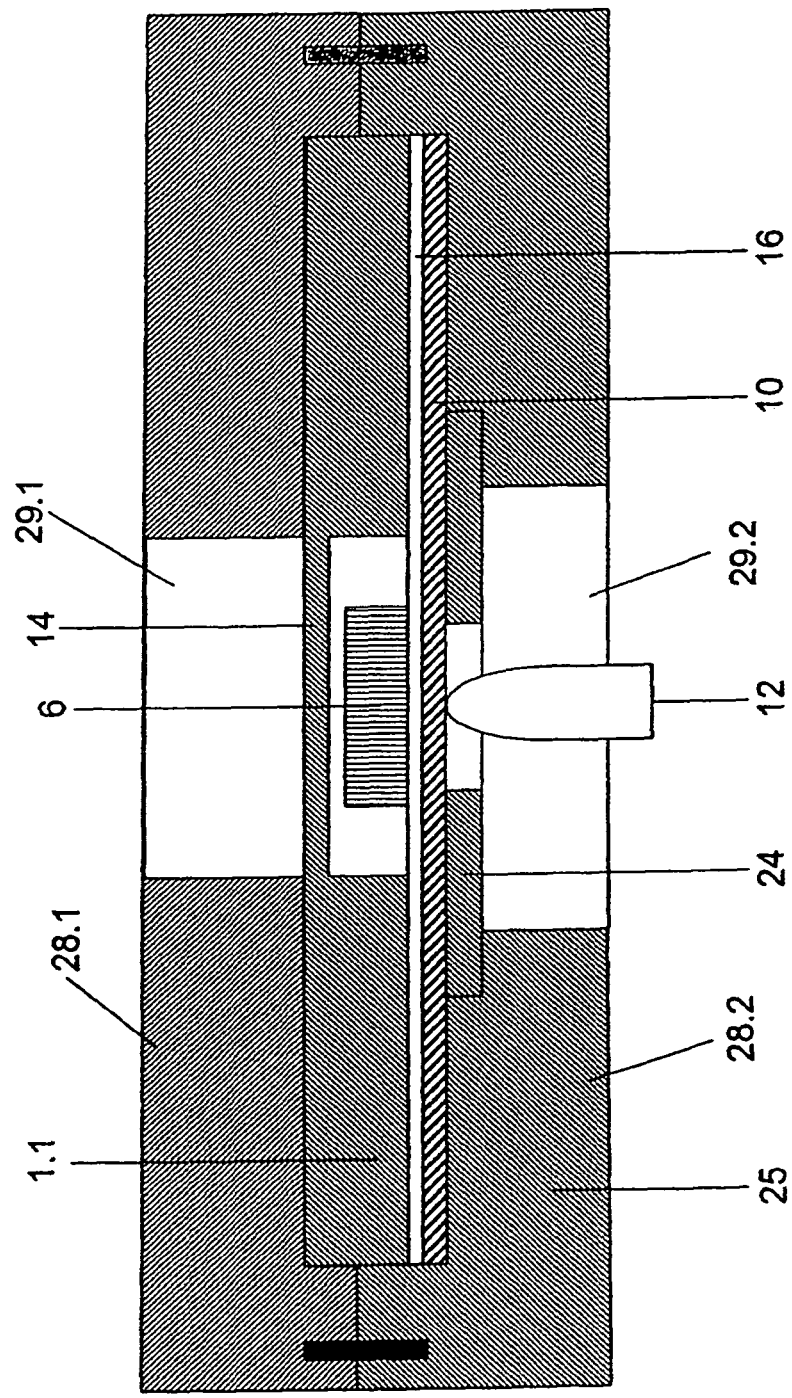
FIG. 12 shows a section through the plug and a filler neck of cartridge II.
Figure 18:
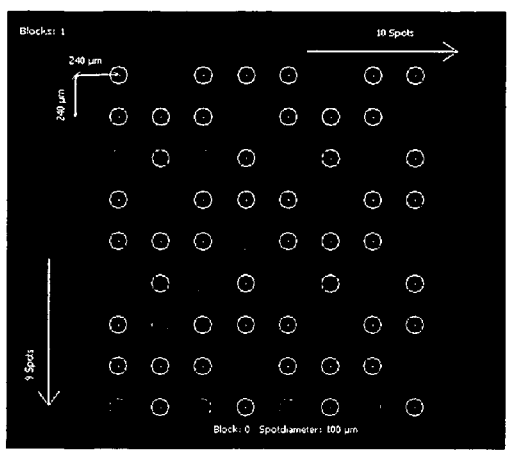
FIG. 18 shows a design drawing biochip-slide.

The coated glass support is cut to a depth of 0.55 mm in a square grid (grid dimension: 3.3 mm) on the front side. The cut grooves subsequently serve as predetermined breaking points when the biochips are to be "separated" before the assembly in the cartridge (FIG. 18).

The cut glass support (external dimensions in the slide format 25×75.6 mm) is functionalized with an epoxy silane (after ultrasound purification with 3-glycidyloxypropyl trimethoxysilane in toluene at 80° C. for 3 h).

Each individual biochip position of the slide is spotted with an identical arrangement of antibodies (array layout). The spotting solution consists of the particular antibody in a concentration of 0.5 mg/ml in 1×PBS and 20 mM trehalose as well as possibly 0.025% BSA. The spotting is effected with a contact-free piezo-nanodispenser (spotter). After spotting, the immobilized antibodies are found in a round area having a diameter of about 130 µm (spot), and the spots are attached at a distance of 200 or 240 µm. A covalent, irreversible linkage of the capture antibodies to the glass support takes place by a reaction of the amino groups of lysine amino acids on the antibody surface with the epoxy groups of the silane coating (FIG. 17).

2. Array Layout

There are 4 categories of spots (83 pieces) in the array layout (FIGS. 14, 15, 16).

Marker (11 spots): Here, amino-modified Cy5-labeled oligonucleotides are spotted which yield permanently shiny spots. These marker spots are automatically identified by the software (alignment) (FIG. 19) and together with the array layout deposited in the software (FIG. 18) serve the assignment of the assessed signal intensities of the spots to the corresponding antibody types.

Capture antibodies (7 pieces as 6-fold replicates): Here, the capture antibodies specific to the particular toxin are spotted. If a corresponding toxin is present, all spots of this type shine after the processing (replicates). In each case, there are 2 different capture antibodies for ricin and SEB as well as 1 capture antibody for BoNT/A, 1 capture antibody for BONT/B and 1 capture antibody of BONT/A and BONT/B.

Positive control (1 as 6-fold replicate): Here, an interleukin antibody (anti-IL-12 rat) is spotted which together with the interleukin IL 12 (mouse) available in the biomix and a further rat interleukin antibody (various clones) builds up a sandwich. Since this sandwich can be build up with every detection, this serves as a functionality control. If the positive control does not supply a signal, a negative test result may not be assessed. Thus, false-positive results can be excluded in the detection.

Negative control (4 pieces as 6-fold replicate): Here, the IgGs isolated from serum are spotted, which are derived from the animal species immunized for the antibody production. If an agent present in the sample to be investigated binds e.g. in non-specific fashion to all antibodies of a certain animal species, the corresponding negative control will also yield a signal. Thus, false-positive results can be excluded in the detection.

The biochip slides are stored in cooled fashion in a nitrogen atmosphere.

3. Cartridge

Central part is an injection-cast body ("inlay") made of a cycloolefin copolymer (Zeonex, Zeonor or Tpoas). The material is highly hydrophobic and has a low surface energy so that there are no problems as regards the adsorption of the biological constituents on the surface of the reaction vessel. Inserted in the surface are structures which define a sample space (with optical window), a pressure compensation space, a filling opening and channels as a communication between said compartments.

The second constituent is a flexible pc board which contains a heating structure as well as a memory chip for cartridge-relevant data and contact islands for the electronic control and read-out of the flex pc board in the device.

This flexible pc board is adhered by means of a double-sided biocompatible adhesive tape ("ARcare 8932" from Adhesives Research), the biochip is placed on the heating structure and the flex pc board is adhered to the inlay. The structures in the inlay thus yield a hermetically sealed interior containing the biochip whose temperature can be controlled via the flexible heating structure.

The inlay is accommodated in two semi-shells which are made of injection-molded plastics and together form the cartridge. In the optic-side semi-shell, a square aperture opening is inserted which is directed in centered fashion to the biochip disposed in the sample space. On the outer side of the semi-shells there are structures which ensure a simple and accurate automatic positioning of the cartridge when inserted in the device.

4. Biomix Tube

The biomix contains the fluorescence-labeled detection antibodies, the PBS buffer constituents and trehalose. A mixture of 40 µl water, containing 10 mM PBS, 100 mM trehalose and 0.5% BSA, with 4 Cy5-labeled detection antibodies (2-15 µg/ml), the Cy5-labeled interleukin-12 antibody (2 µg/ml) and interleukin-12 (400 ng/ml) is directly lyophilized in Eppendorf tubes.

| DAK | Antigen | Antibody |
| --- | --- | --- |
| 1 | Anti-RCA | mAK |
| 2 | Anti-BoNT/A | mAk |
| 3 | Anti-BoNT/A, B | F(ab)2 - fragment |
| 4 | Anti-SEB | mAK |
| 5 | Anti-IL-12 | mAK |

Trehalose is again contained here as well to minimize the load of the antibodies by the lyphilization procedure as well as to ensure the durability of the lyophilizate.

5. Assay Buffer

The assay buffer consists of water and 0.5% Triton X-100. It is used to reconstitute the lyphilisate prior to the sample addition. The Triton X as a non-ionic detergent effects the rapid dissolution of the lyophilisate (trehalose=uncharged disaccharide) and in the filled cartridge also the rapid dissolution of the dried-up spots.

6. Device

The device is controlled via an external PC including software which controls all of the components of the device in fully automated fashion and which can be operated via the installed screen.

An opening is disposed behind a front cover to accommodate the cartridge. An opto-electromechanical module is build up around this cartridge support which accomplishes the temperature control of the sample chamber during processing, the abutment of the biochip against the optical window and the image recording in the fluorescence channel.

When the end user software running on the device is employed, the user interaction is confined to the insertion of the cartridge and the starting of the processing by pushing a button. No further interaction is required up to the display of the final result. For the development of the assay and the service, the device can be externally controlled via TCP/IP.

A suitable device can be purchased from the company Zenteris GmbH, for example.

7. Course of the Application in Detail (Investigation of the Sample)

Figure 19:
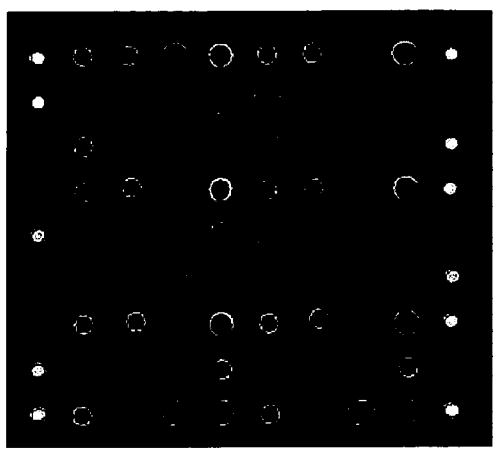
FIG. 19 shows an array layout deposited in software.

Provision of reagents (Biomix tube, assay buffer), Gilson Microman pipette 100 µl, pipette tip, cartridge, start of the device;

Reconstitution of the lyophilized biomix with 20 µl assay buffer;

Addition of 20 µl sample (sample matrix: water) to the biomix=>mixing;

Application of the 40 µl with the pipette into the cartridge;

Open front cover, insert cartridge in the device, close front cover;

Start of processing, typical process parameters are: incubation at 37° C. for 30 minutes;

After a concluded incubation, the biochip is forced against the optical window and a picture is taken in the fluorescence channel. Typical exposure time: 10 seconds;

When the device has produced an image, the automated assessment is started by the software (FIGS. 19, 20).

Discovery of the marker spots.

Alignment of the array layout by means of the marker spots.

Discovery of the antibody spots by means of the disposed array layout.

Calculation of the signal intensities of each spot (median value).

Calculation of the signal intensities of the local background of each spot (median).

Difference formation signal—background.

Classification of the spot quality. "Doubtful" spots are excluded from the further evaluation.

Summary of all of the antibodies of an antigen to be detected by mean value formation.

Assessment of the positive and negative controls for a statement on the validity of the detection: if toxins are detected, the negative control must be negative, if no toxins are detected, the positive control must be active.

The signal intensity of the antigen to be detected must exceed a certain threshold value (assay-specific, determined during the development) and comply with statistical criteria to be deemed as a positive assay.

This result is then displayed on the display screen (FIG. 24).

Figure 21:
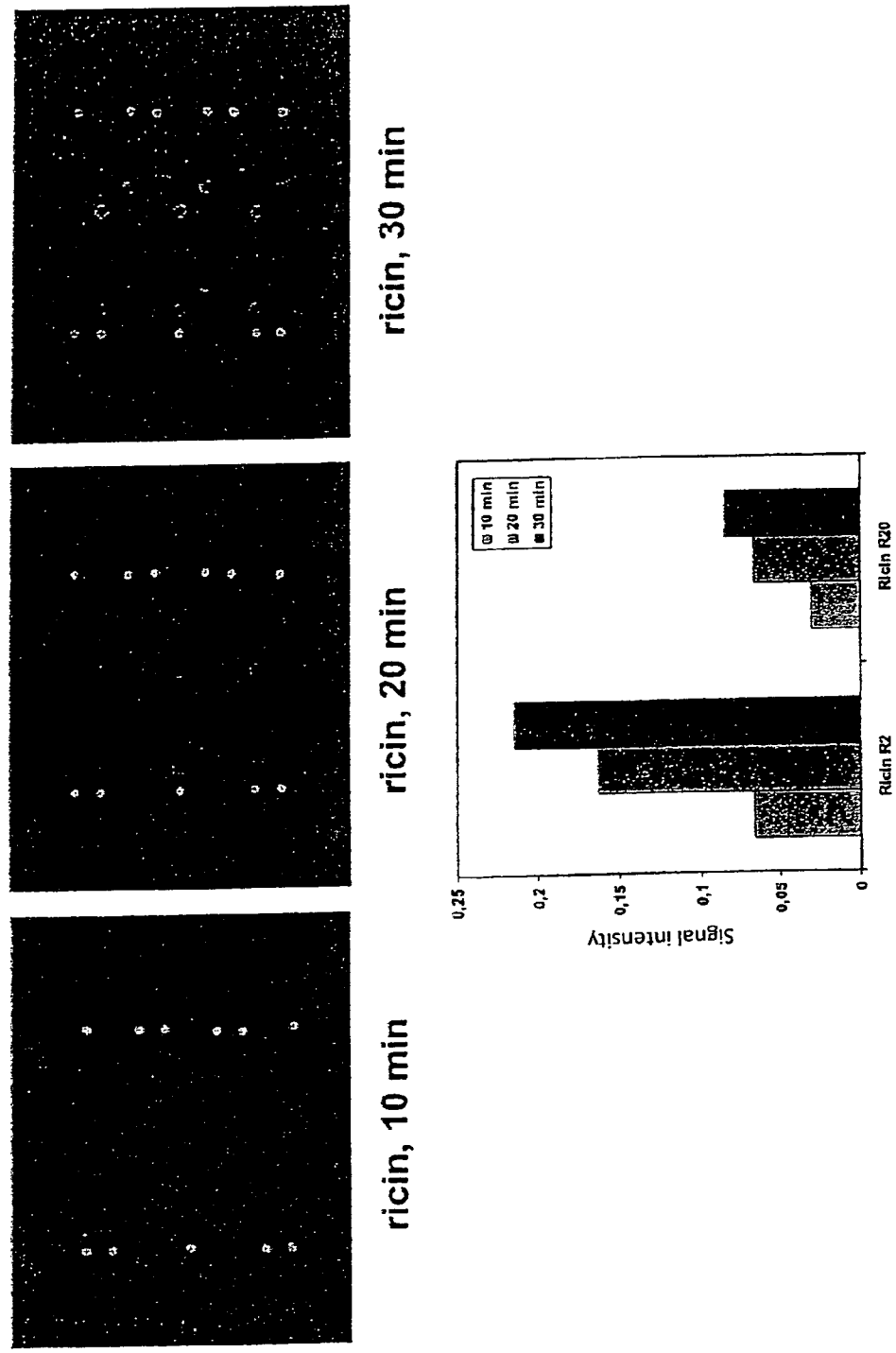
FIG. 21 shows the image of the biochip in the device, evaluation of the intensities.

Evaluation of the results (FIG. 21).

The advantage of the employed process in the light of all the other known processes is that after the start of processing no further interaction is necessary by the user.

Example 2

Time Kinetics Ricin Detection

The conduction of the experiment is described, in principle, as in Example 1. The selected test conditions are:

The same for all 3 experiments:

Detection antibody batch (lyophilized):

| | |
|---|---|
| 1 | (final concentration 9 µg/ml) |
| 2 | (final concentration 1.5 µg/ml) |
| 3 | (final concentration 7.5 µg/ml) |
| 4 | (final concentration 1.9 µg/ml) |
| 5 | (final concentration 3 µg/ml) |
| interleukin 12 | (final concentration 400 ng/ml) |

Lyophilisate in 0.5% triton X in distilled water
Addition of ricin RCA 60 (final concentration 100 ng/ml)
40 µl in cartridge, incubation at 37° C.
Variation of the incubation period: 10, 20, 30 minutes
Image recording and detection of the signal intensity of the ricin capture antibodies.
Means of the intensities (median).
The results are shown in FIG. 22.

Example 3

4-Plex Assay

Dry Run:
Detection antibody batch (fresh solutions, no lyophilisate)

| | |
|---|---|
| 1 | (final concentration 9 µg/ml) |
| 2 | (final concentration 3 µg/ml) |
| 3 | (final concentration 8.25 µg/ml) |
| 4 | (final concentration 1.2 µg/ml) |

Addition of PBS/0.5% BSA, triton X-100 (0.25%)
40 µl in cartridge, incubation at 37° C., incubation time: 30 minutes
Image recording
4-Plex Assay:
Detection antibody batch (fresh solutions, no lyophilisate)

| | |
|---|---|
| 1 | (final concentration 9 µg/ml) |
| 2 | (final concentration 3 µg/ml) |
| 3 | (final concentration 8.25 µg/ml) |
| 4 | (final concentration 1.2 µg/ml) |
| 5 | (final concentration 1.25 µg/ml) |
| Interleukin 12 | (final concentration 400 ng/ml) |

Addition of PBS/0.5% BSA, triton X-100 (0.25%)
Addition of RCA 60 (final concentration 1 µg/ml), SEB (final concentration 1 µg/ml), BONT A complex (final concentration 1 µg/ml), BONT B complex (final concentration 1 µg/ml)

40 µl in cartridge, incubation at 37° C., incubation period: 30 minute

Image recording

The 4-plex detection provides comparable results with ricin crude extract, SEB, BONT A and BONT B culture supernatants.

Figure 23:
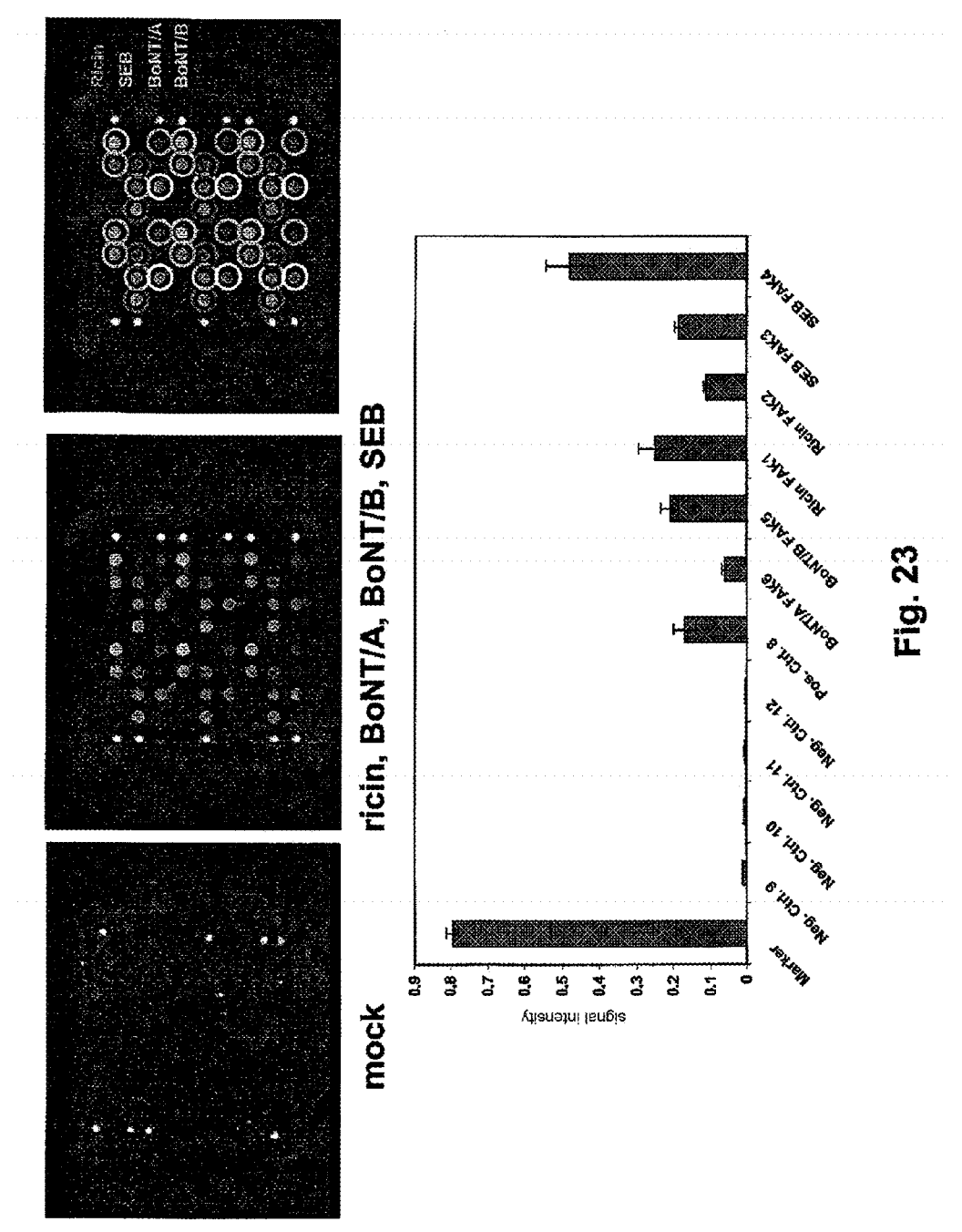

The results are shown in FIG. 23.

Example 4

LOD Determination for SEB Toxin (LOD=Limit of Detection)

The detection limit of this toxin is determined by means of the concentration series of the SEB toxin.

The conduction of the experiment is described, in principle, as in Example 1.

Detection body batch (lyophilized):

| | |
|---|---|
| 1 | (final concentration 13.5 µg/ml) |
| 2 | (final concentration 4.5 µg/ml) |
| 3 | (final concentration 8.25 µg/ml) |
| 4 | (final concentration 1.9 µg/ml) |
| 5 | (final concentration 1.9 µg/ml) |
| interleukin 12 | (final concentration 50 ng/ml) |
| BSA | (final concentration 0.5%) |
| D(+) trehalose | (final concentration 10 mM) |
| PBS | (final concentration 10 mM) |

Lyophilisate in 20 µl water with 0.5% triton X+20 µl ultra-pure water reconstituted addition of various SEC concentrations between 8 ng and 165 µg (dissolved in 10 mM PBS with 0.1% BSA)

40 µl in cartridge, incubation at 37° C. for 30 minutes picture recording, evaluation determination of the LOD value from sigmoidal fit of the intensity values Result: detection limit is 4 ng/ml for SEB The result of the measured values including sigmoidal fit is shown by way of diagram in FIG. 25.

LIST OF REFERENCE NUMBERS 1 base body or base plate
2 compensation space
3 control window or viewing window
4 compensation channel or communicating channel
5 reaction space or sample space
6 biochip
6.1—reaction area (spots)
6.2—rear coating
7 filling channel
8 check valve
9 filling opening or filler neck
10 flex pc board
10.3 heating structure flex pc board
12 tappet
14 detection plane
15 inspection window
27. optical module
101 cartridge
102 housing
103 base wall
104 side wall
105 longitudinal side
106 front side
107 inner side
108 pc board
109 outer side
110 filler neck
111 filling section
112 compaction section
113 chamfer
114 sealing point
115 plug
116 cylindrical section
117 funnel-shaped section
118 filling opening
119 level indicator
120 filling line section
121 through opening
122 reaction space
123 compensation line section
124 compensation space
125 through bore
126 semi-sphere
127 level indicator
128 film
129 gasket
130 biochip
131 sealing ring
132 heating/measuring structure
137 pc board track
138 contact point
139 contact point
140 sampling chamber
141 sample side
142 blade
143 recess
144 centering pin
145 stop
146 optics
147 lens
148 compressed-air line
149 detection device
150 compressed-air supply source
151 aperture

The invention claimed is:

1. A system for immunological detection of specific target molecules in a sample liquid, comprising:
a biotest mixture tube containing a detection binding partner comprising a dye molecule, buffer constituents, at least one detergent and at least one stabilizer, wherein the stabilizer is trehalose;
a single-use cartridge including,
a filling nozzle and filling channel attached thereto;
a biochip comprising a number of M-N reaction areas, wherein at least one known capture antibody or capture antigen is affixed to the reaction areas to bind to the specific target molecules in the sample liquid and wherein one side of the biochip is an optically opaque side;
a reaction space which contains the biochip;
a compensation space connected to the reaction space via a compensation channel;
a pressure-tight sealing valve connected to the filling channel to provide for an excess pressure in the reaction space after filling of the sample liquid;
a temperature control device for adjusting different temperatures to allow the specific target molecule to selectively bind to the reaction areas on the biochip;
a flexible pc board wherein the optically opaque side of the biochip is adhered thereto;

a detection window serving for optically detecting the dye molecules bound to the biochip after an immune reaction by means of an optical module;

a tappet that is positioned to make contact with the flexible pc board thereby overcoming the excess pressure in the reaction space to press the biochip to the detection window for the optical module to detect the dye molecule bound to the biochip and force unreacted sample liquid and the excess pressure into the compensation space and on release of the tappet the excess pressure in the compensation space forces the sample liquid back into the reaction space for additional testing.

2. The system according to claim 1, wherein the biotest mixture tube further contains at least one protein and/or positive control.

3. The system according to claim 1, wherein the detection binding partner is a detection antibody or detection antigen directed against the specific target molecules.

4. The system according to claim 3, wherein the detection antibody or the detection antigen is labeled with the dye molecule, wherein the dye molecule is a fluorescent dye.

5. The system according to claim 3, wherein the detection antibody is biotinylated and the biotest mixture tube further contains streptavidin provided with the dye molecule.

6. The system according to claim 1, wherein the specific target molecules to be detected are proteins, ligands, receptors, viruses, bacteria, medicaments, chemical substances, mycotoxins or toxins.

7. A method for the immunological detection of specific target molecules using the system according to claim 1, comprising the steps of:

adding the sample liquid, which contains the specific target molecules, to the biotest mixture tube to form a mixture;

introducing the mixture into the reaction space of the single-use cartridge;

inserting the single-use cartridge in a device and starting an incubation process;

mechanically displacing the mixture disposed over the biochip after the incubation process is concluded by activating the tappet against the flexible pc board and recording an image by means of an optical module;

evaluating spot intensities of the image by means of software available in the device; and providing a statement on the presence of the specific target molecules.

8. The method according to claim 7, wherein the incubation process takes place between 30° C. and 40° C.

* * * * *